United States Patent [19]

Sia et al.

[11] Patent Number: 5,800,822
[45] Date of Patent: Sep. 1, 1998

[54] TANDEM SYNTHETIC HIV-1 PEPTIDES

[75] Inventors: Charles D. Y. Sia, Thornhill; Pele Chong, Richmond Hill; Michel H. Klein, Willowdale, all of Canada

[73] Assignee: Connaught Laboratories Limited, Willowdale, Canada

[21] Appl. No.: 465,217

[22] Filed: Jun. 5, 1995

Related U.S. Application Data

[63] Continuation of Ser. No. 257,528, Jun. 9, 1994, Pat. No. 5,639,854, which is a continuation-in-part of Ser. No. 73,378, Jun. 9, 1993, abandoned.

[51] Int. Cl.$^6$ .................... A61K 39/21; A61K 39/00; C07K 5/00; C07K 7/00
[52] U.S. Cl. .................... 424/208.1; 424/204.1; 424/184.1; 424/188.1; 530/350; 530/324; 530/327
[58] Field of Search ............... 424/204.1, 208.1, 424/188.1; 530/350, 324, 327

[56] References Cited

U.S. PATENT DOCUMENTS

| | | | |
|---|---|---|---|
| 4,925,784 | 5/1990 | Crowl et al. | 435/5 |
| 5,019,387 | 5/1991 | Haynes | 530/326 |
| 5,229,490 | 7/1993 | Tam | 530/324 |

FOREIGN PATENT DOCUMENTS

| | | |
|---|---|---|
| 90/13564 | 11/1990 | WIPO. |
| 92/22641 | 12/1992 | WIPO. |

OTHER PUBLICATIONS

Sia et al, "Construction of Immunogenic Synthetic HIV Vaccine Candidates"; Proceedings of the International Conference on AIDS, Rome, IT, 1992 see Abstract M.A. 68.
Sia et al, "Construction of Synthetic HIV Vaccine Candidates"; Final Program and Oral Abstracts, vol. 8, No. 1, Abstract No. WeD1039; VII International Conference on AIDS/II STD World Congress, Amsterdam, the Netherlands, 19–24 Jul. 1992.
Luo et al, "Chimeric gag–V3 virus–like particles of human immunodeficeincy virus induce virus–neutralizing antibodies" Proc. Natl. Acad. Sci. USA, vol. 89, pp. 10527–10531 – Nov. 1992.
Tam, J.P. "Synthetic peptide vaccine design: Synthesis and properties of a high–density multiple antigenic pepetide system"; Proc. Natl. Acad. Sci. USA, vol. 85, pp. 5409–5414, Aug. 1988.
Nick et al. "Indentification of HIV–1 env and gag Immunogenic Epitopes Using Sequence–Homologous Synthetic Peptide" AIDS–Forschung 6(9): 467–473 (1991).
Shoeman et al. "Comparison of Recombinant Human Immunodeficiency Virus gag Precursor and gag/env Fusion Proteins and a Synthetic env Peptide as Diagnostic Reagents" Anal. Bioch. 161, 370–379 (1987).
Kenealy et al: "Analysis of human Serum Antibodies to Human Immunodeficiency Virus (HIV) Using Recombinant ENV and GAG antigens" AIDS Res. and Human Retrov., vol. 3, No. 3: 95–105 (1987).
Cohen: Jitters Jeopardize AIDS Vaccine Trials, Science, vol. 262, pp. 980–981 (Nov. 1993).

Norley et al: "Vaccination against HIV", Immunol., vol. 184, pp. 193–207 (1992).
Palker et al: "Polyvalent Human Immunodeficiency Virus Synthetic Immunogen comprised of Envelope gp120 T Helper Cell Sites and B Cell Neutralization Epitopes" J. of Immunology, vol. 142, No. 10: 3612–3619 (1989).
Spalding, B. J. Biotechnology 10: 24–29, 1992.
Papsidero, L. P., Sheu, M. and Ruscetti, F. W. J. Virol. 63: 267–272, 1988.
Sarin, P. S., Sun, D. K., Thornton, A. H. Naylor, P. H. and Goldstein, A. L. Science 232: 1135–1137, 1986.
Palker, T.J. et al., J. of Immunol. 142: 3612–3619, 1989.
Gorny, M. K., Xu, J–Y., Gianakakos, V., Karkowska, S., Williams, C., Sheppard, H. W., Hanson, C. V. and Zolla–Pasner, S. Proc. Natl. Acad. Sci., USA, 88: 3238–3242, 1991.
Buchacher, A. et al, AIDS Research and Human Retroviruses, 10: 359–369, 1994.
Skinner, M. A., Langlois, A. J., Mcdanal, C. B., McDougal, J. S., Bolognesi, D. and Matthews, T. J. J. Virol. 62: 4195–4200, 1988.
Tam, J. P. Proc. Natl. Acad. Sci., USA. 85: 5409–5413, 1988.
Sondergard–Andersen, J. et al. Journal of Immunlogical Methods 131: 99–104, 1990.
O'Hagan (1992), Clin. Pharmokinet 22:1.
Ulmer et al (1993), Curr. Opinion Invest. Drugs 2(9):983–989.
Nick et al. "Identification of HIV–1 env and gag Immunogenic Epitopes Using Sequence–Homologous Synthetic Peptides" AIDS–Forschung 6 (9):467–473 (1991).
Shoeman et al. "Comparison of Recombinant Human Immunodeficiency Virus gag Precursor and gag/env Fusion Proteins and a Synthetic env Peptide as Diagnostic Reagents" Anal. Bioch. 161, 370–379 (1987).
Kenealy et al: "Analysis of Human Serum Antibodies to Human Immunodeficiency Virus (HIV) Using Recombinant ENV and GAG antigens" Aids Res. and Human Retrov., vol. 3, No. 1: 95–105 (1987).
Cohen: Jitters Jeopardize AIDS Vaccine Trials, Science, vol. 262, pp. 980–981 (Nov. 1993).
Norley et al: "Vaccination against HIV", Immunobiol, vol. 184, pp. 193–207 (1992).
Palker et al: "Polyvalent Human Immunodeficiency Virus Synthetic Immunogen comprised of Envelpe gp120 T Helper Cell Sites and B Cell Neutralization Epitopes" J. of Immunology, vol. 142, No. 10: 3612–3619 (1989).
Sia, 1991, "Structure and Immunogenicity of Synthetic HIV Tandem Epitopes" Sixieme Colloques Des Cent. Gardes, pp. 105–110.

*Primary Examiner*—Lynette F. Smith
*Attorney, Agent, or Firm*—Sim & McBurney

[57] ABSTRACT

Novel synthetic peptides are provided which are candidate vaccines against HIV-1 and which are useful in diagnostic application. The peptides comprise an amino acid sequence of a T-cell epitope of the gag protein of HIV-1, specifically p24E linked directly to an amino acid sequence of a B-cell epitope of the V3 loop protein of an HIV-1 isolate and containing the sequence GPGR, and/or the gp41 containing the sequence ELKDWA. Multimeric forms of the tandem synthetic peptides are provided.

9 Claims, 3 Drawing Sheets

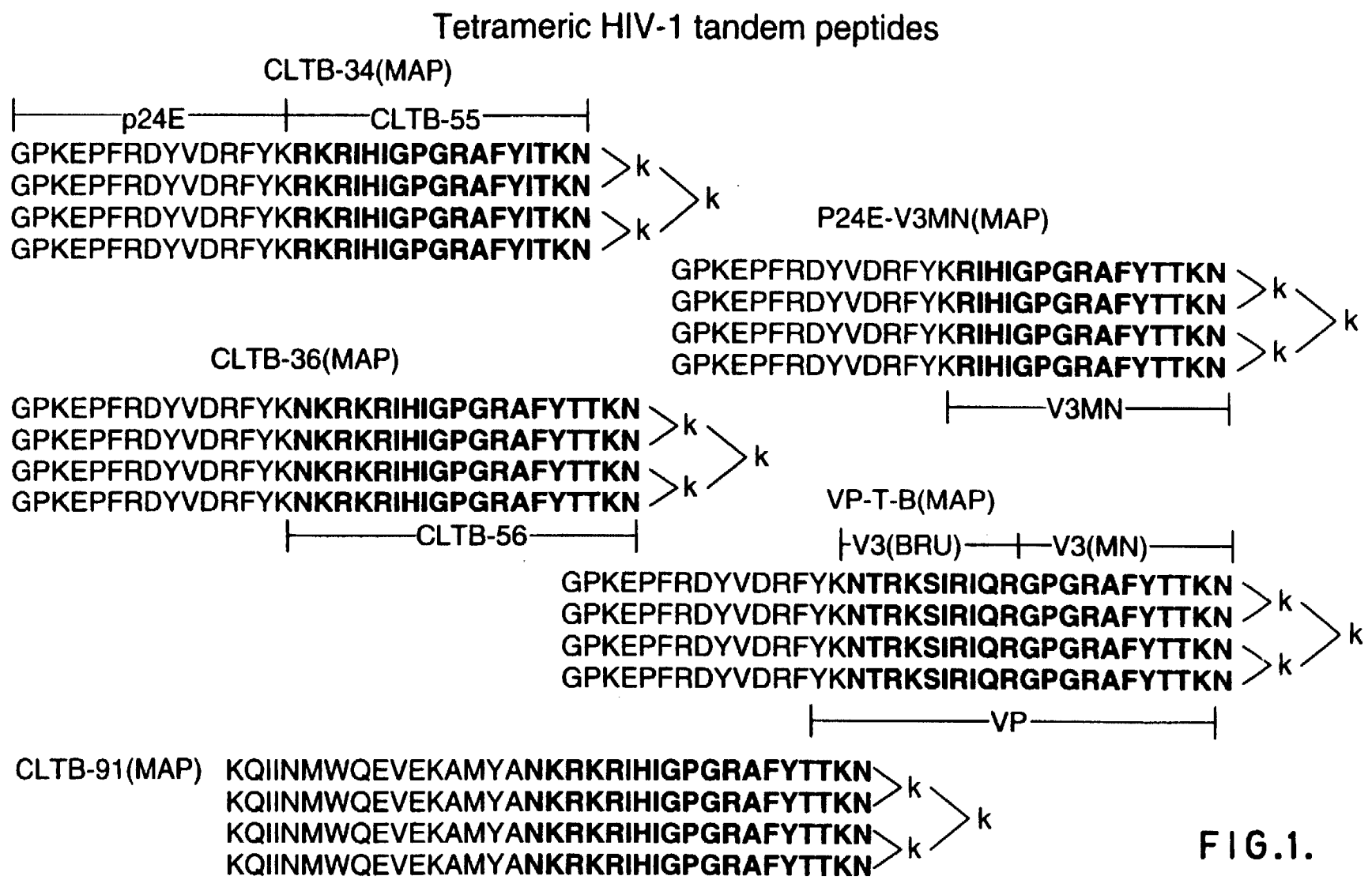

Tetrameric HIV-1 tandem peptides

```
         ┌── CLTB-55 ──────────────┐
┌─

Antibody responses of guinea pigs immunized with HIV-1(IIB) pseudovirion emulsified in incomplete Freund's adjuvant followed by boosting with a HIV-1peptide cocktail formulated in alum Guinea pigs were injected three times with HIV-1 pseudoparticle (MHA at 40 ug equivalent of p24 per dose) emulsified in incomplate Freund's adjuvant at the times indicated. They were then boosted three times with a HIV-1 peptide cocktail consisting of 200 ug of each of the peptides: CLTB-36, CLTB-70, CLTB-91 and CLTB-84, simultaneously adsorbed to 1.5 mg of aluminium phosphate (alum) as indicated. The antibody responses generated against CLTB-56 and CLTB-71 during the course of immunization were shown. Results were expressed as mean titres of three animals.

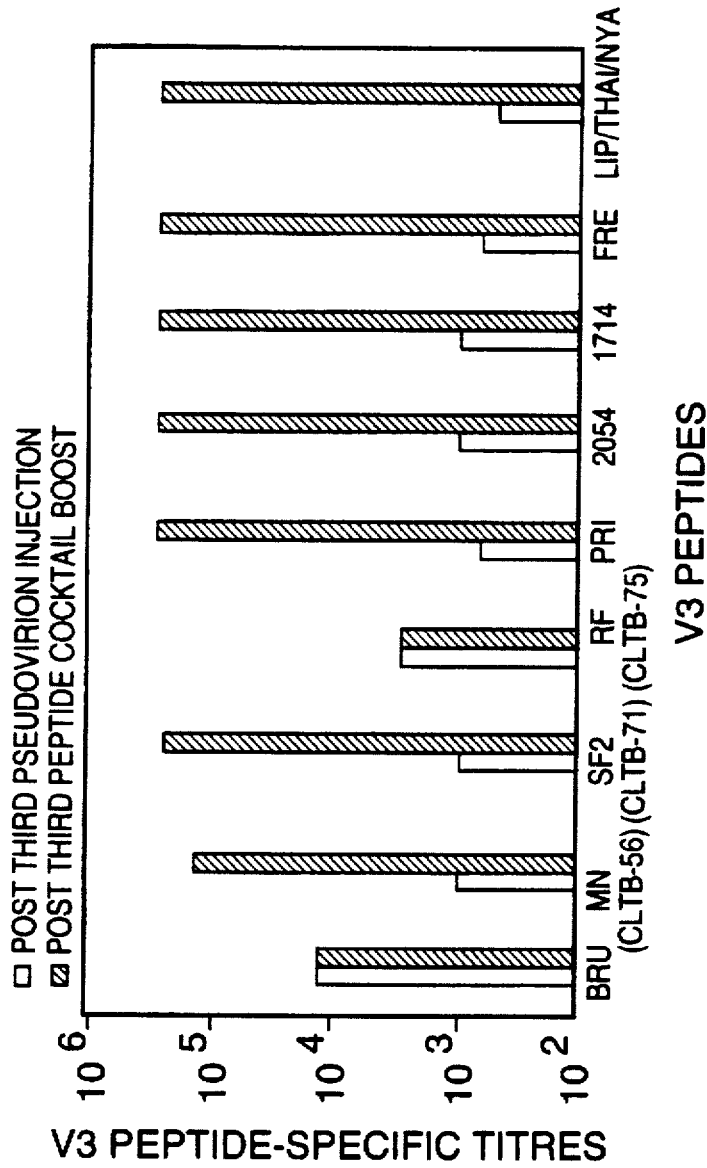

… # TANDEM SYNTHETIC HIV-1 PEPTIDES

REFERENCE TO RELATED APPLICATION

This is a continuation of application Ser. No. 08/257,528 filed Jun. 9, 1994 now U.S. Pat. No. 5,639,854, which is a continuation-in-part of U.S. patent application Ser. No. 073,378 filed Jun. 9, 1993 now abandoned.

FIELD OF INVENTION

The present invention :relates to the field of immunology, and, in particular, is concerned with synthetic peptides containing T- and B-cell epitopes from human immunodeficiency virus proteins.

BACKGROUND TO TITLE INVENTION

AIDS is a disease which is the ultimate result of infection with human immunodeficiency virus (HIV). Currently, there is no effective vaccine which can protect the human population from HIV infection, so the development of an efficacious HIV-vaccine is urgently required. Previously, HIV-1 particles exhaustively inactivated by chemical treatments, a vaccinia vector encoding the whole envelope protein (gp160) of HIV-1, and purified recombinant gp120 have been evaluated as candidate HIV vaccines. Although inactivated HIV-1 virus preparations elicited a T-cell-mediated Delayed-Type Hypersensitivity (DTH) reaction in humans, and vaccinia/gp160 and gp120 recombinant vaccine candidates induced virus neutralizing antibodies, none of these immunogens has been shown to be an efficacious human HIV vaccine (ref. 1—the literature references referred to herein are listed at the end of the specification).

The inventors' interest in HIV vaccinology is to develop synthetic HIV-1 peptides for incorporation into vaccines and consider that the vaccinia HIV-1-recombinant subunit used in conjunction with these HIV-1 peptide vaccines may lead to the elicitation of more effective immune responses against HIV-1. To design synthetic HIV vaccine candidates, immunogenic viral B-cell neutralization epitopes (BE) containing a high degree of conserved sequence between viral isolates are linked to functional T-helper cell determinant(s) (THD) to elicit a strong and long lasting cross-protective antibody response. In addition, HIV-specific cytotoxic T-lymphocyte (CTL) epitopes may be included in the synthetic constructions to elicit cell-mediated immunity to HIV infection.

A specific and preferential spatial relationship between certain T- and B-cell epitopes may be necessary for tandem epitopes to be efficiently processed and thereby rendered immunogenic. Thus, it is important to identify the appropriate T- and B-cell epitope sequences in HIV-1 proteins and assemble them in the optimal configuration so that both T- and B-cell memory can be elicited effectively and antibodies of the desired specificity produced. THDs have been found not to be universal and are immunologically functional only when presented in association with the appropriate Major Histocompatibility Complex (MHC) class II antigens. There is a characteristic hierarchy of T-cell epitope dominance. To develop an effective synthetic AIDS vaccine, it is therefore important to utilize the most potent THD of the various HIV-1 gp160, gag, pol and other gene products. Recent studies have indicated that the gag gene products may play a crucial role in eliciting an immune response against HIV infection. Thus, clinical progression of AIDS is associated with a reduction of circulatory antibodies to the gag p24 protein and antibodies raised against an immunodominant gag p17 peptide are capable of inhabiting HIV-1 infection in vitro (refs. 2, 3).

In our published International Patent Application WO 90/13564, there are described the identification and characterization of a T-cell epitope of the core protein, p24E of HIV-1 and the construction of synthetic chimeric peptides comprising the amino acid sequence of the T-cell epitope linked to an amino acid sequence of a B-cell epitope of an envelope or core protein of HIV-1. By linking the B-cell epitopes to the T-cell epitopes, an immune response to the B-cell epitope was induced, whereas no such response was observed when the B-cell epitope was not so linked. Data are presented in such published application with respect to the p24 T-cell epitope, BE3 epitope, ENV epitope and V3A epitope, all derived from the HIV-1/LAV isolate, with and without linker sequences between the epitopes.

Specific constructs which are tested in the published Wo specification are BE3 linked to the C-terminal end of p24E by direct coupling or to the N-terminal end of the p24E either by two proline residues or by direct coupling. ENV linked to the N-terminal end and linked to the C-terminal end of p24E in both cases by two proline residues, and V3A linked to the N-terminal end and end of p24 by two proline residues.

The V3A sequence tested in that publication (residues 308-327) of the variable loop of HIV-1 gp120 from HIV-1/LAV isolate was made immunogenic by linking the molecule to the N-terminas of p24E with a proline-proline linker.

It is known from U.S. Pat. No. 4,925,784 (Crowl) to provide by recombinant means a fusion protein comprising amino acids 15 to 512 from the gag protein and 44 to 140 of the env protein of the LAV isolate of HIV-I (HTLV-III), i.e., a polypeptide or protein containing 1093 amino acids, considerably longer than any synthetic peptide, which do not exceed 150 amino acids in length and generally are not more than 50 amino acids long. Such large molecule fusion proteins are described as being useful in diagnostic applications and vaccine materials.

The envelope glycoprotein (env) of human immunodeficiency virus (HIV) is highly variable between independent isolates and also sequential isolates from a single infected individual. The amino acid variability in env is concentrated into specific variable regions (mostly in the surface portion gp120 generated by the proteolytic maturation of the initial gp160 gene product), with other regions being less variable. However, the most variable regions often contain neutralizing epitopes so that the virus partially evades the host's immune response and establishes a persistent infection. This variability presents problems for diagnostic techniques based upon specific interactions, with separate or mixed reagents usually being employed to test samples for HIV-1. This variability also presents problems for any possible vaccine or immune therapy, since any suitable agent will have to give a response towards the many strains of HIV-1.

Thus, in generating an immune response in a host to a plurality of immunologically distinct HIV isolates, two problems exist. Firstly, any particular host in an outbred population will have a particular HLA haplotype and will thus differentially respond to a particular T-cell epitope. Secondly, antibodies may not recognize or neutralize a plurality of immunologically distinct HIV isolates and in particular HIV isolates that have been freshly harvested from patients as primary field isolates.

It would be advantageous to provide for the purposes of diagnosis, generation of immunological reagents, treatment and vaccination against HIV, synthetic peptides comprising T-cell epitopes to which a plurality of hosts will respond and B-cell epitopes from protein of different HIV isolates including primary field isolates.

SUMMARY OF THE INVENTION

The present invention is directed towards the provision of synthetic peptides, specifically synthetic HIV-1 peptides, useful for mounting an immune response against infection by HIV or for detecting HIV infection, wherein the synthetic HIV-1 peptides comprise a T-helper determinant (T-cell epitope) of the HIV-1 core protein, particularly p24E of amino acid sequence GPKEPFRDYVDRFYK (SEQ ID NO: 2), and amino acid sequences corresponding to B-cell epitopes from HIV-1 proteins, specifically gp160, gag and pol proteins, vaccines against AIDS comprising at least one of such synthetic HIV-1 peptides and compositions, procedures and diagnostic kits for detecting HIV antigens using such synthetic HIV-1 peptides.

By the term "Synthetic Peptide" as used herein, there is meant the joining of a T-cell epitope containing amino acid sequence to a B-cell epitope containing amino acid sequence to form a synthetic T-B or B-T construct, using, for example, a peptide synthesis process, such as described in Example 1 below.

The prevalent HIV-1 strain found in the AIDS population of North America and Western Europe belongs to the HIV-1(MN) isolate. A synthetic HIV vaccine capable of protecting against this serotype, therefore, may contain p24E as THD and the neutralization epitopes of the HIV-1(MN) proteins as B-cell epitopes. Two regions or epitope clusters in the extracellular component of the HIV-1(MN) envelope protein, gp120, have been shown to elicit neutralizing antibodies against the virus. One of these regions is the third hypervariable (V3) loop encompassing the amino acid residues 301 to 335 of the gp120(MN) (Reference 4). Strain and group-specific monoclonal antibodies isolated from individuals infected with the MN isolate were shown to recognize different core amino acid sequences at the crown region of the V3 loop (Reference 5).

The other epitope cluster of gp120 that elicits neutralizing antibodies is the CD4 binding site. Studies with monoclonal antibodies isolated from HIV-1 infected individuals and chimpanzees have indicated that the neutralization epitopes in the CD4 binding site are formed by noncontiguous amino acid residues from multiple sites of gp120.

Moreover, results on these two types of neutralizing antibodies have shown that the, in vitro neutralization of a given dose of HIV-1 virus may be achieved by a much lower concentration of V3-specific neutralizing monoclonal antibody than of one reacting against the CD4 binding site.

In the construction of synthetic peptides of the present invention, the inventors have chemically synthesized a panel of linear synthetic HIV-1(MN) peptides (shown in Table I below—the Tables appear at the end of the descriptive text) containing different flanking sequences adjacent to the highly conserved sequence (GPGR-SEQ ID NO: 1) at the crown region of the V3(MN) loop, linked either to the amino (N-) or carboxy (C-) terminus of the THD, p24E (GPKEPFRDYVDRFYK-SEQ ID NO: 2). In addition, the inventors have synthesized additional panels of linear synthetic peptides (as shown in Tables VI, VII, IX, X and XI below).

In addition, five tetrameric peptides as depicted in FIG. 1 in which B-cell epitope containing sequences were linked to the C-terminus of p24E, have been prepared and investigated, namely p24E-V3MN(MAP) containing the linear p24E-V3MN sequence; CLTB34(MAP), containing the linear CLTB-34 sequence; CLTB-36(MAP), containing the linear CLTB-36 sequence; CLTB-91(MAP), containing the linear CLTB-91 sequence; and VP-T-B(MAP), containing the linear VP sequence (see FIG. 1); each VP sequence comprising a hybrid V3 sequence of the residues 307 to 316 and 315 to 325 of HIV-1(Mb) and HIV-1(BRU) isolates, respectively, linked to the C-terminus of p24E.

In accordance with one aspect of the present invention, there is provided a synthetic peptide, which comprises at least one amino acid sequence comprising a T-cell epitope of the gag protein of a human immunodeficiency virus (HIV) isolate linked at the N-terminal or C-terminal end thereof, to at least one amino acid sequence comprising a B-(cell epitope of the V3 loop of the envelope protein of an HIV isolate, wherein, when located at said N-terminal end, the B-cell epitope containing sequence and the T-cell epitope containing sequence are directly coupled. Such synthetic peptides are novel and not disclosed in the aforementioned WO 90/13564.

In accordance with another aspect of the present invention, there is provided a synthetic peptide, which comprises at least one amino acid sequence comprising a T-cell epitope of the gag protein of a human immunodeficiency virus (HIV) isolate linked at the N-terminal or C-terminal end thereof, to at least one amino acid sequence comprising a B-cell epitope of the gp41 protein of an HIV isolate comprising the sequence $X_1$LKDW$X_2$ wherein $X_1$ is E, A, G or Q and $X_2$ is A or T, particularly ELKDWA, (see reference 10) or a sequence capable of eliciting an HIV specific antiserum and recognizing the sequence $X_1$LKDW$X_2$. Such synthetic peptides are novel and not disclosed in the aforementioned WO 90/13564.

A further aspect of the invention provides the synthetic peptide molecule, comprising a plurality of individual chimeric synthetic peptides linked to form a multimeric molecule, each said individual synthetic peptide comprising an amino acid comprising a T-cell epitope of a gag or envelope protein of a human immunodeficiency virus (HIV) isolate linked to an amino acid sequence comprising a B-cell epitope of a gag or envelope protein of an HIV isolate. Such multimeric molecules are novel and not disclosed in the aforementioned WO 90/13564.

The invention further comprises antibodies specific to any of the synthetic peptides provided herein and nucleic acid sequences coding for a synthetic peptide as provided herein, which nucleic acid sequences may be incorporated into an expression vector.

The HIV isolate with which the present invention is concerned generally is an HIV-1 isolate. The amino acid sequences of the synthetic peptides comprising the sequences of the T-cell and B-cell epitope containing sequences may be those of a variety of HIV-1 isolates, including LAV, BRU, MN, SF2, RF, PRI, 1714, 2054, HXB2, Z6, BX08, IIIB and SC. Consensus sequences of different isolates also may be employed.

In the embodiment of the invention where the B-cell epitope-containing amino acid sequence is from the V3 loop protein, the amino acid sequence preferably comprises the sequence G$X_1$G$X_2$ where $X_1$ is P or Z and $X_2$ is R, K or Q or a sequence capable of eliciting an HIV-specific antiserum and recognizing the sequence G$X_1$G$X_2$, particularly the sequence GPGR. The B-cell epitope containing sequence may comprise a B-cell epitope containing V3 loop sequences from at least two different HIV-1 isolates and may comprise a consensus sequence of the V3 loop of at least two HIV-1 primary isolates.

In the various embodiments of the invention, the T-cell epitope containing amino acid sequence preferably comprises the sequence of a p24 protein, for example P24E, P24N, P24L, P24M and P24H, particularly P24E. The sequences of those peptides, which are highly conserved among HIV-1 isolates, are given below in Tables I and IX. Such sequences also include a portion, variation or mutant of any of the selected sequences which retains the T-cell properties of the selected sequence.

The amino acid sequence comprising the B-cell epitope may be directly coupled to the C-terminal amino acid of the amino acid sequence comprising the T-cell epitope.

The B-cell epitope containing sequence may be additionally linked to a further amino acid sequence containing an HIV T-cell epitope, which may be that of a gag or envelope protein of HIV. The B-cell epitope containing sequence also may be linked to a further amino acid sequence containing a B-cell epitope of HIV. B-cell epitopes of the gp41 protein and containing the X₁LKDWX₂ sequence may be joined one to another or with amino acid sequences containing the B-cell epitope of the V3 loop.

The multimeric molecules provided herein may comprise a plurality of identical individual chimeric synthetic peptides and preferably comprise the synthetic peptides defined above.

The present invention further provides an immunogenic composition, comprising an immunoeffective amount of at least one synthetic peptide provided in accordance with the invention or at least one nucleic acid molecule encoding any one of the synthetic peptides, and a pharmaceutically-acceptable carrier therefor. In addition, the present invention provides a method of immunizing a host, preferably a human host, comprising administering thereto an immunogenic composition as provided herein.

The immunogenic composition may comprise a plurality of ones of the synthetic peptides selected to provide an immune response to a plurality of immunologically-distinct HIV-1 isolates and preferably further selected to provide the immune response in a plurality of hosts differentially responsive to any particular T-cell epitope.

A particularly useful "cocktail" of peptides useful in the immunogenic composition comprises the peptides identified as CTLB-36, CTLB-91 and BX08 in the Tables below. This composition may further contain the peptide identified on MPK-2 in Table XI below.

The immunogenic composition may be formulated for mucosal or parenteral administration. The immunogenic composition may further comprise at least one other immunogenic or immunostimulating material, particularly an adjuvant, such as aluminum phosphate or aluminum hydroxide.

The present invention also extends to diagnostic kits useful for detecting HIV specific antibodies in a test sample, the kit comprising:

(a) a surface;

(b) at least one peptide having an amino acid sequence epitopically specific for the HIV-specific antibodies immobilized on the surface and as provided herein;

(c) means for contacting the antibodies and the at least one immunobilized peptide to form a complex; and (d) means for detecting the complex.

In a further aspect oil the invention, there is provided a diagnostic kit for detecting HIV antigen in a test sample, the kit comprising:

(a) a surface;

(b) an antibody epitopically specific and non-cross-reactive for distinct epitopes of the HIV antigen immobilized on the surface and raised to the peptides provided herein;

(c) means for contacting the antibodies and the HIV antigen to form a complex; and (d) means for detecting the complex.

BRIEF DESCRIPTION OF DRAWING

FIG. 1 shows the construction of tetrameric peptides which are capable of eliciting polyclonal antibody responses in mice and/or guinea pigs against HIV-1;

FIG. 3 contains a graphical representation of the reactivity of guinea pig antisera raised after priming with non-infectious, non-replicating HIV-1 (IIIB)-like particles and boosted with an HIV-1 peptide cocktail, as provided in an embodiment hereof.

GENERAL DESCRIPTION OF INVENTION

Figure 2:
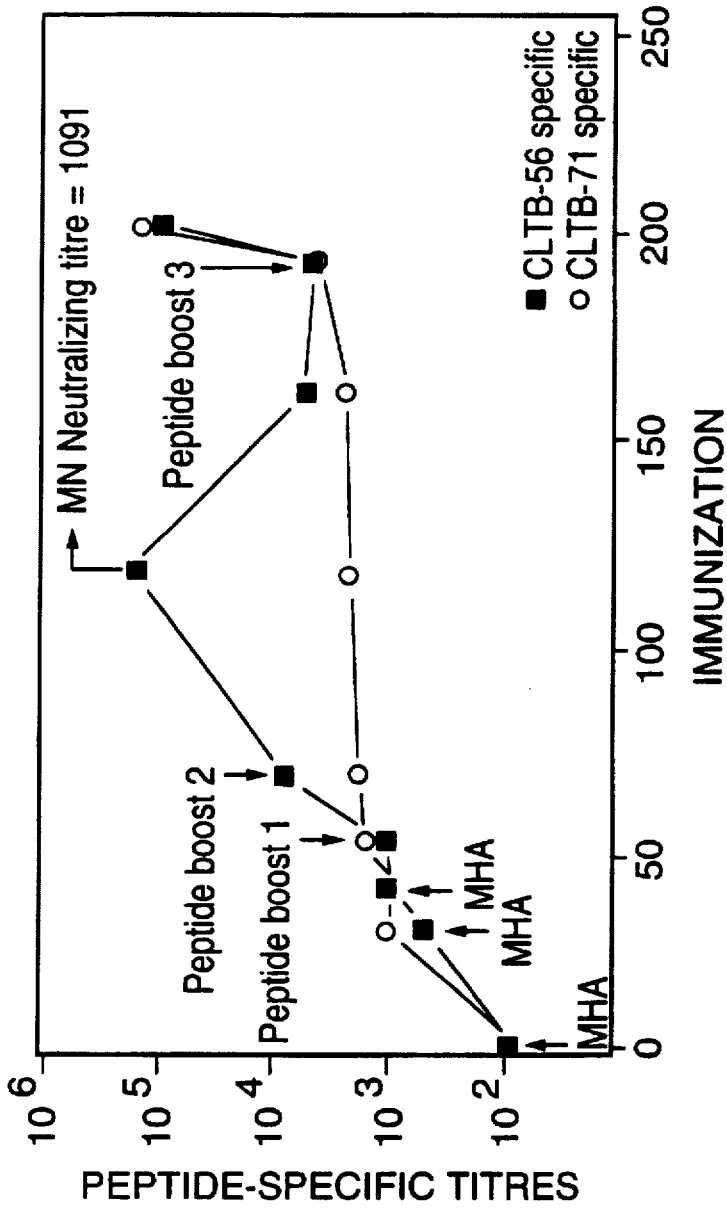
FIG. 2 contains a graphical representation of antibody responses in guinea pigs immunized with non-infectious, non-replicating HIV-1 (IIIB)-like particles followed by boosting with an HIV-1 peptide cocktail, as provided in an embodiment hereof.

In one embodiment, the present invention comprises peptides having amino acid sequence corresponding to antigenic determinants of the V3 loop linked to the N- or C-terminus of the highly conserved T-cell epitope, p24E, of HIV-1 core protein, p24 (as shown in Table I). These peptides can have, for example, the sequence RIHIG-PGRAFYTTKNGPKEPFRDYVDRFYK (V3MN-p24E-SEQ ID NO: 10) and GPKEPFRDYVDRFYKRIHIG-PGRAFYTTKN (p24E-V3MN-SEQ ID NO: 9) corresponding to thus amino acids 311-325 of the V3 (MN) loop printed in bold face (throughout this specification bolded sequences are the B-cell epitope-containing amino acid sequences, unless otherwise noted) linked to the N- and C-terminus of p24E (amino acids 291-305 of the HIV-1 (MN) core protein, p24) as T-cell epitope containing amino acid sequences, respectively. These peptides also can have, for example, the sequence RKRIHIGPGRAFGPKEP-FRDYVDRFYK (CLTB-32-SEQ ID NO: 13) and GPKEP-FRDYVDRFYKRKRIHIGPGRAF (CLTB-28-SEQ ID NO: 12) corresponding to the amino acids 309-320 of the V3(MN) loop printed in bold face linked to the N- and C-terminus of p24E, respectively. These peptides also can have the sequences RKRIHIGPGRAFYTTKNGPKEP-FRDYVDRFYK (CLTB-35-SEQ ID NO: 7) and GPKEP-FRDYVDRFYKRKRIHIGPGRAFYTTKN (CLTB-34-SEQ ID NO: 6) corresponding to the amino acids 309-325 of the V3 (MN) loop printed in bold face linked to the N- and C-terminus of p24E, respectively. The peptides can also have the sequence NKRKRIHIGPGRAFYTTKNGPKEP-FRDYVDRFYK (CLTB-37-SEQ ID NO: 4) and GPKEP-FRDYVDRFYKNKRKRIHIGPGRA FYTTKN (CLTB-36-SEQ ID NO: 3) corresponding to the amino acids 307-325 of the V3 (MN) loop printed in bold face linked to the N- and C-terminus of p24E, respectively.

These peptides are capable of eliciting polyclonal HIV-specific antibody responses in mice, guinea pigs and monkeys (Tables III and IV).

In another embodiment, the present invention comprises multimeric molecules such as the tetrameric peptides (as disclosed in FIG. 1) capable of eliciting polyclonal antibody responses against HIV-1 in mice or guinea pigs (Table XIII). These multimeric molecules, can have, for example, four linear p24E-V3MN sequences (SEQ ID NO: 9) tetramerized using lysine branching peptide synthesis technology, hence designated p24E-V3MN(MAP—multi-antigenic peptide).

These tetramers can also contain, for example, four lysine-branched CLTB-34 sequences (SEQ ID NO: 6), hence designated CLTB-34(MAP). These tetramers can also contain, for example, four lysine-branched CLTB-36 sequences (SEQ ID NO: 3), hence designated CLTB-36 (MAP). These tetramers also may contain, for example, four lysine-branched CLTB-91 sequences (SEQ ID NO: 20) and hence designated CLTB-91(MAP). These tetramers also can contain, for example, four lysine-branched VP-T-B linear sequence, GPKEPFRDYVDRFYKNTRKSIRIQRG-PGRAFYTTKN (SEQ ID NO: 15) comprising a hybrid V3 sequence, VP(NTRKSIRIQRGPGRAFYTTKN-SEQ ID NO: 16), linked to the C-terminus of p24E (SEQ ID NO: 2). The hybrid V3 sequence, VP, itself comprises amino acids 307-316 (NTRKSIRIQR-SEQ ID NO: 17) of the V3(BRU) loop printed in bold face linked via its C-terminal end to the N-terminal end of the amino acid sequence 315-325 (GPGRAFYTTEN-SEQ ID NO: 18) of the V3(MN) loop shown in bold face.

The novel immunogenic compositions of the present invention comprise peptides containing immunogenic T- and B-cell epitopes of HIV, prepared as peptides which link specific antigenic determinants from the extracellular envelope domain, gp120, gp41 and the core protein p24, of HIV-1. These compositions are useful for immunization to elicit HIV-specific humoral immune responses when administered to mammals as demonstrated in mice, guinea pigs and monkeys as seen by the data presented below in the Examples.

Synthesis of peptides

To design a synthetic peptide-based HIV immunogen, linear peptides containing sequences from the V3 loop and gp41 linked to either the N- or C-terminus of peptides containing T-cell epitopes were chemically synthesized using an automated ABI 430A solid-phase peptide synthesizer, as described in Example 1. Different combinations were formulated in Freund's adjuvant (FA) or aluminum phosphate (alum) to compare their ability to induce HIV-specific immune responses in mammals.

Five multimeric molecules, designated p24E-V3MN (MAP), CLTB34(MAP), CLTB-36(MAP), CLTB-91(MAP) and T-B-VP(MAP), formed by tetramerization using lysine branching peptide synthesis technology of the respective linear tandem epitopes, i.e. p24E-V3MN, CLTB-34, CLTB-36, CLTB-91 and VP-T-B also were prepared. Their ability to elicit HIV specific immune responses in mammals when administered in alum or FA was investigated.

Immunogenicity of the linear HIV peptides in mammals

The ability of the linear HIV peptides to elicit antibody responses in mammals was examined by immunizing mice, guinea pigs or monkeys with individual peptides emulsified in FA or adsorbed to alum. After four injections of 100 μg each by the subcutaneous route, IgG antibody responses were determined by peptide-specific EIA and by an in-vitro syncytia-blocking assay (Tables II, III, IV, V, XII).

The four different V3(MN) peptides, namely V3MN, CLTB-29, CLTB-55 and CLTB-56, containing the different sequences flanking the crown portion (GPGR) of the V3(MN) loop but lacking the p24E sequence were either non-immunogenic or poorly immunogenic irrespective of whether they were injected in FA or aluminium phosphate (alum) (see Table III below). The carrier function of p24E to enhance the immunogenicity of these peptides was shown by studies performed with the respective synthetic HIV-1 peptides comprising a T-cell epitope and a B-cell epitope. Thus, the synthetic HIV-1 peptides in the T-B orientation elicited V3(MN)-specific antibody responses of much greater magnitude than the respective free V3(MN) peptides or B-T counterparts (Table III). The results of these studies, therefore, showed that the orientation of the V3(MN) peptide with respect to p24E influenced the immunogenicity of the synthetic HIV-1 peptides of the present invention. A comparison of the respective anti-V3 peptide antibody titres measured in the murine and guinea pig antisera generated against the individual synthetic HIV-1 peptides, administered in either FA or aluminium phosphate (alum), revealed that CLTB-36 was the most immunogenic peptide in both guinea pigs and mice (Table III).

The immunogenicity of CLTB-36 was further demonstrated by the ability of this peptide when formulated in the adjuvant ISA 51 to elicit a strong peptide-specific antibody response in primates (Table IV) which antibodies were virus neutralizing. Significantly, both the murine and guinea pig antisera raised against CLTB-34 and CLTB-36 were able to cross-react against the V3 peptides of a variety of HIV-1 serotypes (Table V below).

The novel usage of p24E and a V3 sequence for the construction of immunogenic T-B peptides is further illustrated by the studies performed with three other chimeric peptides designated p24E-SP10(A), CLTB-91, CLTB-84 and T1-SP10(A)-MN (Table I). The results in Table III below showed that when administered in either FA or alum, p24E-SP10(A) with the sequence GPKEPFRDYVDRFYKCTRPNYNKRKRIHIGPGRAFYTTK (SEQ ID NO: 19), comprising the N-terminal end (CTRPNYNKRKRIHIGPGRAFYTTK-SEQ ID NO: 20) of the V3(MN) loop linked to the C-terminus of p24E was able to induce good titres of CLTB-56-specific antibodies in guinea pigs. p24E-SP10(A) formulated in alum similarly elicited a high anti-CLTB-56 antibody response in Balb/c ($H-2^d$). In constrast, T1-SP10(A)-MN, with the sequence KQIINMWQEVEKAMYACTRPNYNKRKRIHIGPGRAFYTTK-SEQ ID NO: 21), containing the same N-terminal end of the V3(MN) loop linked to the C-terminus of a T-cell epitope, T1 (KQIINMWQEVEKAMYA-SEQ ID NO: 22) reported in the literature (Ref. 4) was found to be poorly immunogenic in guinea pigs and Balb/c ($H-2^d$) mice. These data suggested that p24E served as a more effective carrier for the N-terminal sequence of the V3(MN) loop than T1. Moreover, T1 was found to mediate the enhancement of immunogenicity of CLTB-56. This result was shown by the high CLTB-56-specific antibody titres measured in the serum samples of guinea pigs immunized with the CLTB-91 peptide of the sequence, KQIINMWQEVEKAMYANKIZRIHIGPGRAFYTTKN-SEQ ID NO: 23), comprising of (CLTB-56 linked to the T-cell epitope T1 in FA or alum, and mice injected with CLTB-91 in alum. Since CLTB-91 differs from T1-SP10(A)-MN only in the V3(MN) sequences linked to the C-terminus of T1, these data show that CLTB-56 is a better B-cell epitope than the N-terminal end of V3 (MN) loop used in T1-SP10(A)-(MN). Furthermore, CLTB-84 containing the CLTB-56 sequence linked to the C-terminus of another T-cell epitope, P24M comprising the sequence GHKARVLAEMSQVT (SEQ ID NO: 30) of p24, when administered in alum was also found to be highly immunogenic in guinea pigs (Table III).

Five other panels of HIV-1 synthetic peptides were produced. In the first panel of peptides shown in Table VI (SEQ ID NOS: 38 to 47), the V3 sequences of two different U.S. clinical HIV isolates, 1714 (NTRKRIHAGPGRAFYATGDIIG-SEQ ID NO: 48) and 2054 (NTRKGIHIGPGRAFYTGEIVGDIRQ-SEQ ID NO: 49), were linked to the C-terminus of p24E and T1 to form the p24E-1714 and T1-2054 respectively. In addition, the V3 consensus sequence, PRI(NTRKSIPIGPGRAFYTTG-SEQ ID NO: 50), of the consensus of New York and Amsterdam isolates was linked to either p24E, T1 or p24M to form the respective T-B peptides of CLTB-PRI, T1-PRI and p24M-PRI. Furthermore, three other T-B peptides were constructed by linking p24E to the V3 sequences of LAI (NTRKSIRIQRGPGRAFYTIG-SEQ ID NO: 51), RF(NTRKSITKGPGRVIYATGQIIG-SEQ ID NO: 52) and a hybrid V3 sequence of MN and RF(NKRKRIHIGPGRVIYATGQIIG-SEQ ID NO: 53) to form the respective CLTB-V3B, CLTB-V3RF and CLTB-HB constructs.

A second panel of constructs are shown in Table VII (SEQ ID NOS: 54 to 68). The particular gp41 sequences used for their constructions share the neutralization epitope, ELDKWA (SEQ ID NO: 69), described in reference 6. The results in Table VIII showed that each of these peptides was recognized by the human neutralizing monoclonal antibody, 2F5 (Reference 6).

Table IX shows the third panel of peptides which were constructed (SEQ ID NOS: 70 to 84). The constructions involved the use of the CLTB-56 sequence for linking to either the N- or C-terminus of three different T-cell epitopes from gag namely P24N (QMREPRGSDIAGTTSTL-SEQ ID NO: 70), P24L (EEMMTACQGVGGPGHK-SEQ ID NO: 73) and P24M (GHKARVLAEAMSQVT-SEQ ID NO: 30, 76) to form the B-T or T-B synthetic peptides respectively. Furthermore, the consensus sequence, PRI (NTRKSIPIGPGRAFYTTG-SEQ ID NO: 50, 80) of the New York and Amsterdam isolates was also linked to either the N- or C-terminus of the T-cell epitope, P24H (PIVQNIQGQMVHQKI-SEQ ID NO: 79) or T5 (VKYKVVKIEPLGVAP-SEQ ID NO: 82) to form the respective B-T or T-B peptides.

The fourth panel of peptides made are shown in Table X (SEQ ID NOS: 85 to 92). Peptides CLTB-102 and CLTB-105 were constructs containing a hybrid sequence of gp41 (ELLELDKWASLWNWF-SEQ ID NO: 93) and CLTB-56 linked to the C- and N-terminus of the T-helper epitope, p24E, respectively. CLTB-103 and CLTB-107 are peptides containing the CLTB-56 and the same gp41 sequence linked to the C- and N-terminus of P24E, respectively. For constructs CLTB-160 and CLTB-161, the V3 sequences from a consensus (LIP) of the London, India and Paris isolates, the V3 sequence (THAI) of a Thailand (HIV-1 virus and a consensus of the primary isolates found in New York and Amsterdam) were used to link to the C-terminus of the T-cell epitope, p24E and T1, respectively.

The fifth panel of peptides constructed is shown in Table XI (SEQ ID NOS: 94 to 97). The peptide, MPK-1, contains a copy of the gp41 neutralization epitope (ELDKWAS-SEQ ID NO: 98) linked via a GPG linker sequence at its N- and C-terminus to the T1 and p24E T-cell epitopes respectively. The construction of the peptide, MPK-2, was the same as MPK-1 except that the orientation of T1 and P24E were reversed. The constructions of MPK-3 and MPK-4 involved the use of two copies of the gp41 sequence ELDKWAS for making MPK-1 to link its N- or C-terminus to either T-1 and p24E, or p24E and T1, respectively.

Immunogenicity of HIV-1 peptide cocktail

The immunogenicity of ii cocktail containing five peptides of the present invention was assessed in guinea pigs (Table II). These tandem peptides consisted of: CLTB-70, containing the V3 sequence of the HIV-1(SF2) isolate linked to the C-terminus of p24E; CL T3-72, containing the V3 sequence of HIV-1(IIIB) linked to the C-terminus of p24E; CLTB-74, containing the V3 sequence of HIV-1(RF) linked to the C-terminus of p24E; CLTB-76, containing the V3 sequence of HIV-1(Z6) linked to the C-terminus of p24E and p24E-GP41C, containing a gp41 sequence of HIV-1(BRU) linked to the C-terminus of p24E. The results shown in Table II show that animals immunized with the cocktail formulated in FA or alum elicited high antibody responses against each of the five tandem peptides.

Therefore, the above-described results show the ability of the peptide cocktail when adsorbed to alum to elicit strong antibody responses against the V3 loops of four different HIV-1 isolates (SF2, IIIB, RF and Z6) and a gp41 sequence of HIV-1(BRU).

An immunization schedule using another HIV-1 peptide cocktail consisting of CLTB-36, CLTB-91, CLTB-84 (shown in Table 1) and CLTB-70 (shows in Table II) and an HIV-1 self-assembled, non-replicating, non-infectious HIV-like particle (as described in WO 91/058564 published May 2, 1991) were also investigated. Results depicted in FIG. 2 show that guinea pigs previously immunized with the HIV-like particle emulsified in incomplete Freund's adjuvant and boosted with the cocktail adsorbed to alum were found to elicit strong antibody responses against the CLTB-56 peptide. The virus neutralizing titre of the antisera against the MN isolate following the second booster injection with the cocktail was 1,091. Very significantly, the results depicted in FIG. 3 further show that the antisera collected from the animals post-second boost with the peptide cocktail demonstrated strong cross-reactivity against peptides containing V3 sequences of several laboratory grown viruses and primary clinical isolates.

Other peptide cocktails may comprise immunoeffective amounts of any of the disclosed peptides including a synthetic peptide, which comprises at least one amino acid sequence comprising a T-cell epitope of the gag protein of a human immunodeficiency virus (HIV) isolate linked at the N-terminal or C-terminal end thereof, to at least one amino acid sequence comprising a B-cell epitope of the gp41 protein of an HIV isolate comprising the sequence $X_1LKDWX_2$ wherein $X_1$ is E, A, G or Q and $X_2$ is A or T or a sequence capable of eliciting an HIV-specific antiserum and recognizing the sequence $X_1LKDWX_2$ and in particular peptide MPK-2 (SEQ ID NO. 95, Table XI).

The functional activity of the antisera generated against the synthetic HIV-1 peptides was investigated by testing their ability to inhibit syncytia formation induced by the homologous HIV-1(MN) isolate. The murine antisera following immunization with the four V3 (MN) peptides containing only the B-cell epitope containing sequences, namely V3MN, CLTB-29, CLTB-55 and CLTB-56 administered in either FA or aluminium phosphate (alum), lacked syncytia-blocking-activity (see Table XII below). Guinea pig antisera generated against CLTB-56 formulated in FA, but not aluminium phosphate (alum), were found to inhibit >90% syncytia inhibitory activity at a dilution of 1 in 10. The murine and guinea pig antisera raised against the B-T tandem synthetic peptides namely, V3MN-p24E, CLTB-32 and CLTB-35, in either FA or alum, which showed poor antibody titres reactive against the respective B-cell epitope containing peptides namely, V3MN, CLTB-29 and CLTB-55 were also found to lack syncytia-blocking activity. However, guinea pig antisera generated against CLTB-37 administered in FA or aluminium phosphate (alum), which contained a CLTB-56-specific antibody titre of 1 in 1,250 and 1 in 450, respectively, were both found to have syncytia-inhibition titres of 1 in 10. The results of the functional studies carried out with the antisera raised against the immunogenic T-B synthetic peptides revealed that both murine and guinea pig antisera raised against the T-B synthetic peptide, CLTB-36, in either FA or aluminium phosphate (alum) strongly inhibited syncytia.-formation induced by the homologous (MN) virus. In addition, the antisera raised against CLTB-36 formulated in ISA 51 in cynomolgus monkeys were also found to have good neutralizing titres (278 and 430 in the two animals) against the MN isolate (see Table IV) . The murine4 and guinea pig antisera generated against p24E-V3MN and CLTB-34 in FA containing higher titres of V3MN- and CLTB-55-specific antibodies than the respective antisera raised against the peptide in alum also were found to have effective syncytia—blocking activity. It was also observed that the animal species used for immunization affected the production of V3(MN)-specific functional antibodies. This effect was illustrated, for example, by the fact that, although the T-B tandem synthetic peptide CLTB-28 in FA induced the same titre of anti-CLTB-29 antibodies in mice and guinea pigs, only the antiserum raised in the latter had a high titre of syncytia-inhibition activity.

Immunogenicity of multimeric molecules in mammals

The ability of the multimeric molecules CLTB-36(MAP), CLTB-91(MAP), CLTB-34(MAP), p24E-V3 MN (MAP) and VP-TB(MAP), (with their respective configurations illustrated in FIG. 1) to elicit antibody responses in mammals was examined by immunizing mice and guinea pigs with the molecules emulsified in FA or alum. After four doses each of 100 µg, IgG antibody responses were determined by peptide-specific ELISA and by an in vitro syncytia-blocking assay.

The results of the immunogenicity studies performed with the multimeric molecules in mice and/or guinea pigs are shown in Table XIII below. High titres of CLTB-56-specific peptide antibodies were generated in both mice and guinea pigs immunized with the tetramer CLTB-36 (MAP) in either FA or alum. CLTB-91(MAP) formulated in either FA or alum similarly induced high CLTB-56-specific antibody titres in these animals. The tetrameric T-B tandem synthetic peptide CLTB-34(MAP), p24E-V3MN (MAP) or VPTB (MAP), administered in FA also were capable of eliciting high titres of the respective CLTB-55, V3MN and VP-specific antibodies in guinea pigs. The murine and guinea pig antisera raised against CLTB-36(MAP) in either FA or alum strongly inhibited syncytia formation induced by the HIV-1(MN) virus (Table XIV below). The guinea pig antisera raised against the branched peptides CLTB-34 (MAP) and VP-T-B(MAP) in FA similarly exhibited potent syncytia-blocking activity.

It is clearly apparent to one skilled in the art, that the various embodiments of the present invention have many applications in the fields of vaccination, diagnosis, treatment of HIV infections, and the generation of immunological reagents. A further non-limiting discussion of such uses is further presented below.

Vaccine Preparation and Use

It has been shown that a peptide in accordance with the invention can elicit an immune response. One possible use of the molecule is therefore as the basis of a potential vaccine against AIDS and AIDS related conditions. In a further aspect, the invention thus provides a vaccine against AIDS and AIDS related conditions, comprising a molecule in accordance with the invention.

Immunogenic compositions, suitable to be used as vaccines, may be prepared from immunogenic peptides as disclosed herein. The immunogenic composition elicits an immune response which produces antibodies that are opsonizing or antiviral. Should the vaccinated subject be challenged by HIV, the antibodies bind to the virus and thereby inactivate it.

Vaccines containing peptides are generally well known in the art, as exemplified by U.S. Pat. Nos. 4,601,903; 4,599,231; 4,599,230; and 4,596,792. Vaccines may be prepared as injectables, as liquid solutions or emulsions. The peptides may be mixed with pharmaceutically-acceptable excipients which are compatible with the peptides. Excipients may include water, saline, dextrose, glycerol, ethanol, and combinations thereof. The vaccine may further contain auxiliary substances such as wetting or emulsifying agents, pH buffering agents, or adjuvants to enhance the effectiveness of the vaccines. Methods of achieving adjuvant effect for the vaccine include the use of agents such as aluminum hydroxide or phosphate (alum), commonly used as 0.05 to 0.1 percent solution in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions take the form of solutions, suspensions, tablets, pills, capsules, sustained release formulations or powders and contain 10–95% of the peptides.

The vaccines are administered in a manner compatible with the dosage formulation, and in such amount as is therapeutically effective, protective and immunogenic. The quantity to be administered depends on the subject to be treated, including, for example, the capacity of the individual's immune system to synthesize antibodies, and to produce a cell-mediated immune response. Precise amounts of active ingredient required to be administered depend on the judgment of the practitioner. However, suitable dosage ranges are readily determinable by one skilled in the art and may be of the order of micrograms of the peptides. Suitable regimes for initial administration and booster doses are also variable, but may include an initial administration followed by subsequent administrations, for example, at least one pre-peptide immunization with a self-assembled, non-infectious, non-replicating HIV-like particle, such as described in WO 91/058564, assigned to the assignee hereof, followed by at least one secondary immunization with the peptides provided herein. The dosage of the vaccine may also depend on the route of administration and will vary according to the size of the host.

Nucleic acid molecules encoding the peptides of the present invention may also be used directly for immunization by administration of the nucleic acid molecules directly, for example by injection, or by first constructing a live vector, such as Salmonella, BCG, adenovirus, poxvirus, vaccinia or poliovirus, and administering the vector. A discussion of some live vectors that have been used to carry heterologous antigens to the immune system are discussed in, for example, O'Hagan 1992, (ref. 10). Processes for the direct injection of DNA into test subjects for genetic immunization are described in, for example, Ulmer et al, 1993, (ref. 11).

The use of the peptides provided herein in-vivo may require their modification since the peptides themselves may not have a sufficiently long serum and/or tissue half-life. For this purpose, the molecule of the invention may optionally be linked to a carrier molecule, possibly via chemical groups of amino acids of the conserved sequence or via additional amino acids added at the C- or N-terminus. Many suitable linkages are known, e.g., using the side chains of Tyr residues. Suitable carriers include, e.g., keyhole limpet hemocyanin (KLH), serum albumin, purified protein derivative of tuberculin (PPD), ovalbumin, non-protein carriers and many others.

In addition, it may be advantageous to modify the peptides in order to impose a conformational restraint upon it. This might be useful, for example, to mimic a naturally-occurring conformation of the peptide in the context of the native protein in order to optimize the effector immune responses that are elicited. Modified peptides are referred to herein as "analog" peptides. The term "analog" extends to any functional and/or structural equivalent of a peptide characterized by its increased stability and/or efficacy in-vivo or in-vitro in respect of the practice of the invention. The term "analog" also is used herein to extend to any amino acid derivative of the peptides as described herein.

Analogs of the peptides contemplated herein include, but are not limited to, modifications to side chains, and incorporation of unnatural amino acids and/or their derivatives, non-amino acid monomers and cross-linkers. Other methods which impose conformational constraint on the peptides or their analogs are also contemplated.

It will be apparent that the peptide of the invention can be modified in a variety of different ways without significantly affecting the functionally important immunogenic behaviour thereof. Possible modifications to the peptide sequence may include the following:

One or more individual amino acids can be substituted by amino acids having comparable or similar properties, thus:

V may be substituted by I;

T may be substituted by S;

K may be substituted by R; and

L may be substituted by I, V or M.

One or more of the amino acids of peptides of the invention can be replaced by a "retro-inverso" amino acid, i.e., a bifunctional amine having a functional group corresponding to an amino acid, as discussed in WO 91/13909.

One or more amino acids can be deleted.

Structural analogs mimicking the 3-dimensional structure of the peptide can be used in place of the peptide itself.

Examples of side chain modifications contemplated by the present invention include modification of amino groups, such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6, trinitrobenzene sulfphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatization, for example, to a corresponding amide.

Sulfhydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; and carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tryosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butyglycine, norvaline, phenylglycine, ornithine, sarcosine, 4-amino-3-hydroxy-6-methylheptanoic acid, 2-thienylalanine, and/or D-isomers of amino acids.

Crosslinkers can be-used, for example, to stabilize 3-dimensional conformations, using homo-bifunctional crosslinkers such as the bifunctional imido esters having $(CH_2)_n$, spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio (for SH) or carbodiimide (for COOH). In addition, peptides could be conformationally constrained by, for example, incorporation of α-methylamino acids, introduction of double bonds between adjacent C atoms of amino acids and the formation of cyclic peptides or analogs by introducing covalent bonds such as forming an amide bond between N and C termini, between two side chains or between a side chain and the N or C terminus.

The peptides of the invention or their analogs may occur as single length or as multiple tandem or non-tandem repeats. A single type of peptide or analog may form the repeats or the repeats may be composed of different molecules including suitable carrier molecules.

The immunogenicity of the peptides of the present invention may also be modulated by coupling to fatty acid moieties to produce lipidated peptides. Convenient fatty acid moieties include glycolipid analogs, N-palmityl-S-(2RS)-2, 3-bis-(palmitoyloxy)propyl-cysteinyl-serine ($PAM_3$ Cys-Ser), N-palmityl-S-[2,3 bis (palmitoyloxy)-(2RS)-propyl-[R]-cysteine (TPC) or a dipalmityl-lysine moiety.

The peptides may also be conjugated to a lipidated amino acid, such as an octadecyl ester of an aromatic acid, such as tyrosine, including actadecyl-tryrosine (OTH).

Molecules in accordance with the invention may further find use in the treatment (prophylactic or curative) of AIDS and related conditions, by acting either to displace the binding of the HIV virus to human or animal cells or by disturbing the 3-dimensional organization of the virus.

A further aspect of the invention thus provides a method for the prophylaxis or treatment of AIDS or related conditions, comprising administering an effective amount of a peptide in accordance with the invention.

Immunoassays

The peptides of the present invention are useful as immunogens, as antigens in immunoassays including enzyme-linked immunosorbent assays (ELISA), RIAs and other non-enzyme linked antibody binding assays, or procedures known in the art for the detection of anti-HIV antibodies. In ELISA assays, the peptides are immobilized onto a selected surface, for example a surface capable of binding peptides. such as the wells of a polystyrene microtitre plate. After washing to remove incompletely adsorbed peptides, a non-specific protein, such as a solution of bovine serum albumin (BSA) or casein, that is known to be antigenically neutral with regard to the test sample may be bound to the selected surface. This allows for blocking of non-specific adsorption sites on the immobilizing surface and thus decreases the background caused by non-specific bindings of antisera onto the surface.

In one diagnostic embodiment where it is desirable to identify antibodies that recognize a plurality of HIV isolates, a plurality of peptides of the present invention are immobilized onto the selected surface. Alternatively, when the B-cell epitope of a peptide of the present invention is highly conserved among various HIV isolates (for example, a B-cell epitope from gag or gp41) a single or a limited number of peptides may be immobilized. In a further diagnostic embodiment where it is desirable to specifically identify antibodies that recognize a single HIV isolate (for example, BRU, MN or SF2) a single peptide of the present invention may be immobilized. This further diagnostic embodiment has particular utility in the fields of medicine, clinical trials, law and forensic science where it may be critical to determine the particular HIV isolate that was responsible for the generation of antibodies.

Normally, the peptides are in the range of about 12 residues and up to about 14 to about 40 residues. It is understood that a mixture of peptides may be used either as an immunogen in, for example, a vaccine or as a diagnostic agent. There may be circumstances where a mixture of peptides from conserved regions and/or from the non-conserved regions are used to provide cross-isolate protection and/or diagnosis. In this instance, the mixture of peptide immunogens is commonly referred to as a "cocktail" preparation for use as an immunogenic composition or a diagnostic reagent.

The immobilizing surface is then contacted with a sample, such as clinical or biological materials to be tested, in a manner conducive to immune complex (antigen/antibody) formation. This may include diluting the sample with diluents such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound peptides, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity, such as an enzymatic activity that will generate, for example, a colour development upon incubating with an appropriate chromogenic substrate. Quantification may then be achieved by measuring the degree of colour generation using, for example, a visible spectra spectrophotometer.

Other uses

Molecules which bind to the conserved sequence on which the invention is based, particularly antibodies, antibody-related molecules and structural analogs thereof, are also of possible use as agents in the treatment and diagnosis of AIDS and related conditions.

Variants of antibodies (including an antigen binding site), such as chimeric antibodies, humanized antibodies, veneered antibodies, and engineered antibodies which bind to the peptides of the present invention are included within the scope of the invention.

Antibodies and other molecules which bind to the peptides of the present invention can be used for therapeutic (prophylactic and curative) and diagnostic purposes in a number of different ways, incuding the following:

For passive immunization by suitable administration of antibodies, possibly humanized antibodies, to HIV patients.

To activate, complement or mediate antibody dependent cellular cytotoxicity (ADCC) by use of antibodies of suitable subclass or isotype (possibly obtained by appropriate antibody engineering) to be capable of performing the desired function.

For targeted delivery of toxins or other agents, e.g., by use of immunotoxins comprising conjugates of antibody and a cytotoxic moiety, for binding directly or indirectly to a target conserved sequence of, for example, or gp120 or gp41.

For targeted delivery of highly immunogenic materials to the surface of HIV-infected cells, leading to possible ablation of such cells by either the humoral or cellular immune system of the host.

For detection of HIV, e.g., using a variety of immunoassay techniques.

In yet a further diagnostic embodiment, the peptide of the present invention (individually, or as mixtures including cocktail preparations) are useful for the generation of HIV antigen specific antibodies (including monoclonal antibodies) that can be used to detect HIV or antigens, or neutralize HIV in samples including biological samples.

In an alternative diagnostic embodiment, the peptides of the present invention can be used to specifically stimulate HIV specific T-cells in biological samples from, for example, HIV-infected individuals.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

EXAMPLES

Methods of peptide synthesis, enzyme immunoassays (EIA) and in-vitro syncytia-blocking assay (ref. 7) used by Dr. Thomas Matthews's group at Duke University (North Carolina, U.S.A.) that are not explicitly described in this disclosure are amply reported in the scientific literature and are well within the scope of those skilled in the art.

Example I

This Example illustrates the synthesis of linear peptides.

The peptides shown in Tables I, II, VI, VII, IX, X and XI below were synthesized according to the amino acid sequences reported for the various HIV-1 isolates identified therein using the ABI (Applied Biosystems Inc) 430A peptide synthesizer and optimized t-Boc chemistry as described by the manufacturer. The crude peptides were removed from the resin by treatment with hydrofluoric acid (HF), and purified by reverse-phase high performance liquid chromatography (RP-HPLC) using a Vydac C4 semi-preparative column (1×30 cm) using a 15–55% acetonitrile gradient in 0.10% (v/v) trifluoroacetic acid (TFA) developed over 40 minutes at a flow rate of 2 ml/min. All synthetic peptides (Table I below) used in immunological testing and immunization studies were >95% pure as judged by analytical HPLC. Amino acid composition analyses performed on a Waters Pico-Tag system were in good agreement with the theoretical compositions.

Example II

This Example illustrates the synthesis of branched peptides:

The synthetic branched HIV-1 peptides (MAP) shown in FIG. 1 were prepared using an ABI 430A peptide synthesizer and syntheized according to the method previously described by Tam (ref. 8). The MAP peptides were purified by RP-HPLC as described for the linear peptides in Example I.

Example III

This Example describes the protocol used to test the immunogenicity of the HIV-1 chimeric peptides.

Five 6–12 week old Balb/c (H-2$^d$) mice or three 6–8 week old female Duncan Hartley guinea pigs purchased from Charles River animal farm, Montreal, Canada and Hazleton animal farm, Denver, Co., U.S.A., respectively, were individually immunized with 100 µg of the given free peptide as follows. The animals received the given dose of the peptide emulsified in Freund's complete adjuvant (CFA) or adsorbed to 3 mg of aluminium phosphate (alum) by the subcutaneous route; this was followed with a booster-dose of the same amount of the same peptide emulsified in Freund's incomplete adjuvant (IFA) or adsorbed to 3 mg of aluminium phosphate (alum) three weeks later. The mice were further boosted twice with the same amount of the same peptide prepared in the respective adjuvants at three week intervals. Sera of the experimental mice and guinea pigs collected on the 9th and 14th day post-boosting, respectively, were assayed for peptide-specific IgG antibodies using a standard enzyme-linked immunoabsorbant assay (EIA), and assessed for syncytia-blocking activities.

Example IV

This Example illustrates the testing of anti-peptide antibodies using an Enzyme Immunoassay (EIA).

EIA for the detection of antibodies reactive with the V3 peptide of the different constructs was performed by coating EIA plates (Covalink, Nunc, Denmark) with the respective BE- containing V3 peptides as shown in Table 1 below and FIG. 1 at 1 µg per well according to the procedure described in reference 9. After 30 min. incubation at 4° C., the unbound peptides were removed by washing the plates three times with washing buffer [phosphate-buffered saline (PBS) pH 7.0, containing 0.025% Tween 20 (Bio-rad Laboratories, Richmond, Calif.)]. A three-fold dilution of each of the experimental serum samples starting at 1 in 50 then was made in PBS containing 0.05% skimmed milk, and 100 µl of the diluted serum then was added to each of the peptide-coated wells. Each dilution of the serum samples was assayed in duplicate. Binding of the V3 peptide-specific antibodies to the immobilized peptide was allowed to take place by incubating the plates for 1 hr at room temperature. The unbound antibodies were removed by washing the plates three times with washing buffer. One hundred microliter of goat anti-mouse IgG antibody horse radish peroxidase conjugate (Jackson Lab.,) diluted 1 in 5,000 in washing buffer as recommended by the manufacturer, then were added to each test well to detect the specific binding of the anti-V3 peptide antibody to the target peptide. After one hr of incubation at room temperature, the unbound antibody-conjugate was removed by washing the plates four times with the washing buffer. The amount of bound conjugate was assayed by the addition of 100 µl of a mixture of tetramethylbenzidine (TMB) and hydrogen peroxide (1 part of TMB to 9 parts of hydrogen peroxide as recommended by the manufacturer, ADI Diagnostics Inc., Willowdale, Canada). Colour development was allowed to take place at room temperature in the dark for 10–15 min., and arrested by the addition of 100 µl of 1N sulphuric acid. The optical densities of the enzyme reactions were read on a TITERTEK MULTI SKAN Spectrophotometer (MCC/340 model) at 450 nm. Results are shown in Table III and are expressed as mean reciprocal reactive titres. The reciprocal titres for normal mouse sera, irrespective of the haplotypes, were always <50.

SUMMARY OF DISCLOSURE

In summary of this disclosure, the present invention provides certain synthetic peptides comprising amino acid sequences comprising the T-cell epitopes of the HIV-1 gag protein and amino acid sequences corresponding to the V3 loop of the envelope protein including the GPGR sequence and/or the gp41 protein comprising the ELKDWA sequence, tetrameric forms of such peptides, capable of eliciting an immune response to HIV-1 infection and vaccine compositions comprising such tandem synthetic peptides. Modifications are possible within the scope of this invention.

TABLE I

| HIV-1 Chimeric peptides described in this disclosure | | |
|---|---|---|
| PEPTIDE | SEQUENCE* | SEQ ID NO: |
| p24E | GPKEPFRDYVDRFYK | 2 |
| CLTB-36 (T-B) | GPKEPFRDYVDRFYKNKRKRIHIGPGRAFYTTKN | 3 |
| CLTB-37 (B-T) | NKRKRIHIGPGRAFYTTKNGPKEPFRDYVDRFYK | 4 |
| CLTB-56 (B) | NKRKRIHIGPGRAFYTTKN | 5 |
| CLTB-34 (T-B) | GPKEPFRDYVDRFYKRKRIHIGPGRAFYTTKN | 6 |
| CLTB-35 (B-T) | RKRIHIGPGRAFYTTKNGPKEPFRDYVDRFYK | 7 |
| CLTB-55 (B) | RKRIHIGPGRAFYTTKN | 8 |
| p24E-V3MN (T-B) | GPKEPFRDYVDRFYKRIHIGPGRAFYTTKN | 9 |
| V3MN-p24E (B-T) | RIHIGPGRAFYTTKNGPKEPFRDYVDRFYK | 10 |
| V3MN (B) | RIHIGPGRAFYTTkN | 11 |

TABLE I-continued

HIV-1 Chimeric peptides described in this disclosure

| PEPTIDE | SEQUENCE* | SEQ ID NO: |
|---|---|---|
| CLTB-28 (T-B) | GPKEPFRDYVDRFYKRKRIHIGPGRAF | 12 |
| CLTB-32 (B-T) | RKRIHIGPGRLFGPKEPFRDYVDRFYK | 13 |
| CLTB-29 (B) | RKRIHIGPGRAF | 14 |
| p24E-SP10 (A) | GPKEPFRDYVDRFYKCTRPNYNKRKRIHIGPGRAFYTTK | 19 |
| CLTB-91 | KQIINMWQEVEKAMYANKRKRIHIGPGRAFYTTKN | 23 |
| T1-SP10 (A) MN | KQIINMWQEVEKAMYACTRPNYNKRKRIHIGPGRAFYTTK | 21 |
| CLTB-84 (T-B) | GHKAVLAEMSVTNKRKRIHIGPGRAFYTTKN | 29 |

*V3 (MN) sequence used to construct each of the tandem epitopes in either T-B or B-T orientation is printed in bold face.

TABLE II

Immunogenicity of HIV-1 peptide cocktail in guinea pigs

| Peptide Cocktail | Sequence | Anti-peptide* IgG titre Freund's | Anti-peptide* IgG titre Alum | SEQ ID NO: |
|---|---|---|---|---|
| CLTB-70 + | GPKEPFRDYVDRFYKNTRKSIYIGPGRAFHTTGR | 312,500 | 25,000 | 24 |
| CLTB-72 + | GPKEPFRDYVDRFYKNTRKRIRIQRGPGRAFVTIGK | 312,500 | 25,000 | 25 |
| CLTB-74 + | GPKEPFRDYVDRFYKNTRKSITKGPGRVIYATGQ | 625,000 | 62,500 | 26 |
| CLTB-76 + | GPKEPFRDYVDRFYKNTRQSTPIGLGQALYTTRG | 625,000 | 12,500 | 27 |
| p24E-GP41C | GPKEPFRDYVDRFYKSLIEESQNQQEKNEQELLELDKWAS | 625,000 | 12,500 | 28 |

*Guinea pigs were primed and boosted four times with the cocktail formulated in FA or alum. Antisera were assayed against the individually T-B tandem epitopes used to make the cocktail. Results represented the mean titre of three guinea pigs immunized with a cocktail of five different HIV-1 tandem epitopes formulated in either Freund's adjuvant or alum. The cocktail consists of: CLTB-70 (SEQ ID NO: 24), containing the V3 sequence of SF2 linked to the C-terminus of: p24E; CLTB-72 (SEQ ID NO: 25), containing the V3 sequence of IIIB linked to the C-terminus of p24E; CLTB-74 (SEQ ID NO: 26), containing the V3 sequence of RF linked to the C-terminus of p24E; CLTB-76 (SEQ ID NO: 27), containing the V3 sequence of Z6 linked to the C-terminus of p24E and p24E-GP41C (SEQ ID NO: 28), containing the gp41 sequence of HIV-1(BRU) linked to the C-terminus of p24E.

TABLE III

Immunogenicity of HIV-1 peptides

| Immunizing Peptide | | Reciprocal V3(MN) peptide-specific antibody titre* Murine Freund's | Murine Alum | Guinea Pig Freund's | Guinea Pig Alum |
|---|---|---|---|---|---|
| CLTB-36 | (T-B) | 328,050 | 109,350 | 109,350 | 12,150 |
| CLTB-37 | (B-T) | 12,150 | 1,250 | 12,150 | 450 |
| CLTB-56 | (B) | 450 | 150 | 1,250 | 450 |
| CLTB-34 | (T-B) | 109,350 | 12,150 | 109,350 | 12,150 |
| CLTB-35 | (B-T) | 450 | 450 | 1,250 | 900 |
| CLTB-55 | (B) | 50 | 50 | 450 | 150 |
| p24E-V3MN | (T-B) | 36,450 | 1,250 | 36,450 | 2,700 |
| V3MN-p24E | (B-T) | 450 | 450 | 1,250 | 900 |
| V3MN | (B) | <50 | <50 | 150 | 150 |
| CLTB-28 | (T-B) | 36,450 | 4,050 | 36,450 | 1,250 |
| CLTB-32 | (B-T) | 150 | 150 | 12,150 | 450 |
| CLTB-29 | (B) | <50 | <50 | 50 | 50 |
| p24E-SP10(A) | | NC | 24,300 | 2,700 | 2,700 |
| CLTB-91 | | NC | 145,800 | 58,600 | 8,100 |
| CLTB-84 | | | | 108,000 | 48,600 |
| T1SP10(A)-MN | | 300 | 100 | 900 | 300 |

*Represented as the mean reciprocal antibody titre reactive against the individual envelope BE-containing V3(MN) peptide of sera from five Balb/c (H-2d) and three Duncan Hartly Guinea Pigs immunized with the respective peptide formulated in the adjuvant indicated.
NC = not completed.

TABLE IV

Immunogenicity of CLTB-36 in Cynomolgus Monkeys*

| Monkey Number | Dose (ug) | Adjuvant | CLTB-36-specific Titre | Neutralizing Titre (MN) |
|---|---|---|---|---|
| 14039 | 200 | ISA 51 | 25,600 | 278 |
| 14040 | 200 | ISA 51 | 12,800 | 430 |

*Monkeys were immunized intramuscularly with 200 ug of CLTB-36 emulsified in Montanide ISA 51 (Seppic) on days 0, 28 and 84. Sera collected two weeks post second boost (i.e immunization on day 84) were assayed.

TABLE V

EIA reactivities of anti-CLTB-34 and anti-CLTB-36 antisera against V3 peptides

| V3 peptide Sequence | SEQ ID NO: | Iso-late | Titre Anti-CLTB-34* Mur-ine | Anti-CLTB-34* G.Pig | Anti-CLTB-36* Mur-ine | Anti-CLTB-36* G.Pig |
|---|---|---|---|---|---|---|
| RKRIHIGPGRAF | 31 | MN | 4,050 | 4,050 | 4,050 | 4,050 |
| TRSIHIGPGRAF | 32 | SC | 1,350 | 4,050 | 4,050 | 4,050 |
| RRRIHIGPGRAF | 33 | JH3 | 4,050 | 4,050 | 4,050 | 4,050 |
| RKSIYIGPGRAF | 34 | SF2 | 1,350 | 450 | 1,350 | 450 |
| KSIRIQRGPGRAFVTIG | 35 | LAI | 450 | 4,050 | 450 | 4,050 |

TABLE V-continued

EIA reactivities of anti-CLTB-34 and anti-CLTB-36 antisera against V3 peptides

| V3 peptide Sequence | SEQ ID NO: | Iso-late | Anti-CLTB-34* Murine | Anti-CLTB-34* G.Pig | Anti-CLTB-36* Murine | Anti-CLTB-36* G.Pig |
|---|---|---|---|---|---|---|
| RKRIRIQRGPGRAF | 36 | HXB2 | 150 | 1,350 | 150 | 1,350 |
| RKSITKGPGRVIYAT | 37 | RF | 50 | 50 | 50 | 50 |

*Antisera were raised in Balb/c mice: and guinea pigs by subcutaneous injection of 100 ug of CLTB-34 or CLTB-36 adsorbed to 1.5 mg of aluminium phosphate (alum). Results represented mean of four mouse and three guinea pig serum samples post the fourth injection.

TABLE VIII

Reactivity of human monoclonal antibody 2F5 against HIV-1 peptides containing the gp41 neutralization epitope

| Peptide* | Absorbance (450 nm)# |
|---|---|
| CLTB-106 (negative Control) | 0.07 |
| CLTB-92 | 0.63 |
| CLTB-92A | 0.22 |
| CLTB-93 | 0.51 |
| CLTB-94 | 0.34 |
| CLTB-95 | 0.25 |
| CLTB-96 | 0.14 |
| CLTB-97 | 0.54 |
| CLTB-98 | 0.58 |
| CLTB-99 | 0.32 |
| CLTB-100 | 0.61 |
| CLTB-101 | 0.48 |

TABLE VI

| Peptide | Sequence* | Isolate Origin. of V3 sequence | SEQ ID NO: |
|---|---|---|---|
| CLTB-V3B | GPKEPFRDYVDRFYKNTRKSIRIQRGPGRAFYTIG | LAI | 38 |
| CLTB-V3RF | GPKEPFRDYVDRFYKNTRKSITKGPGRVIYATGQIIG ---- MN ---- | RF | 39 |
| CLTB-HB | GPKEPFRDYVDRFYKNKRKRIHIGPGRVIYATGQIIG --- RF --- | MN/RFhybrid | 40 |
| CLTB-PRI | GPKEPFRDYVDRFYKNTRKSIPIGPGRAFYTTG | Consensus of New York and Amsterdam | 41 |
| P24E-1714 | GPKEPFRDYVDRFYKNTRKRIHMGPGRAFYATGDIIG | U.S. clinical isolate | 42 |
| P24E-FRE | GPKEPFRDYVDRFYKNTRKSIHIGPGRAFYTTGEIIGC | Consensus of French | 43 |
| CLTB-BX08 | GPKEPFRDYVDRFYKNTRKSIHIGPGRAFYATGEIIG | French primary | 44 |
| T1-PRI | KQIINMWQEVEKAMYANTRKSIPIGPGRAFYTTG | Consensus of New York and Amsterdam | 45 |
| T1-2054 | KQIINMWQEVEKAMYANTRKGIHIGPGRAFYTGEIVGDIRQ | U. S. clinical isolate | 46 |
| P24N-PRI | GHKARVLAEAMSQVTNTKRSIPIGPGRAFYTG | Consensus of New York and Amsterdam | 47 |

*The V3 sequence used for the construction of the individual tandem epitope peptide is bolded whereas those of the T-cell epitopes, p24E(GPKEPFRDYVDRFYK - SEQ ID NO: 2), T1 (KQIINMWQEVEKAMYA - SEQ ID NO: 22) and p24M (GHKARVLAEAMSQVT -SEQ ID NO:77) are shown in plain letters.

TABLE VII

| Peptide | Sequence* | SEQ ID NO: |
|---|---|---|
| CLTB-92 | GPKEPFRDYVDRFYKEQELLELDKWASLWNWFDIT | 54 |
| CLTB-92A | EQELLELDKWASLWNWFDIT | 55 |
| CLTB-93 | GPKEPFRDYVDRFYKELLELDKWASLWNWFDIT | 56 |
| CLTB-94 | ELLELDKWASLWNWFDIT | 57 |
| CLTB-95 | GPKEPFRDYVDRFYKELDKWASLWNWFDIT | 58 |
| CLTB-96 | ELDKWASLWNWFDIT | 59 |
| CLTB-97 | GPKEPFRDYVDRFYKEQELLELDKWASLWNWF | 60 |
| CLTB-97A | EQELLELDKWASLWNWF | 61 |
| LTB-98 | GPKEPFRDYVDRFYKELIELDKWASLWNWF | 62 |
| CLTB-99 | GPKEPFRDYVDRFYKELKWASLWNWF | 63 |
| CLTB-100 | GPKEPFRDYVDRFYKEQELLELDKWA | 64 |
| CLTB-101 | GPKEPFRDYVDRFYKELLELDKWA | 65 |
| T1-KAT1 | KQIINMWQEVEKAMYAEQELLELDKWASLWNWF | 66 |
| T1-KAT2 | KQIINMWQEVEKAMYAELDKWAS | 67 |
| T1-KAT3 | KQIINMWQEVEKAMYAGPGELLELDKWASL | 68 |

*gp41 sequence containing Katinger's neutralization epitope (ELDKWA - SEQ ID NO: 69) used for the construction of the respective tandem epitope peptide is bolded whereas the T-cell epitopes, p24E (GPKEPFRDYVDRFYK - SEQ ID NO: 2) and T1 (KQIINMWQEVEKAMYA - SEQ ID NO: 22) are shown in plain letters.

TABLE VIII-continued

Reactivity of human monoclonal antibody 2F5 against HIV-1 peptides containing the gp41 neutralization epitope

| Peptide* | Absorbance (450 nm)# |
|---|---|
| CLTB-102 | 0.65 |
| CLTB-103 | 0.71 |
| CLTB-105 | 0.65 |
| CLTB-107 | 0.55 |
| MPK-1 | 0.77 |
| MPK-2 | 0.72 |
| MPK-3 | 0.76 |
| T1-KAT 1 | 0.54 |
| T1-KAT 2 | 0.62 |
| T1-KAT 3 | 0.77 |

*The sequences of the peptides are shown in Tables IV, VI and VIII. Each individual peptide was coated at 1 µg per well of an ELISA plate. Human neutralizing monoclonal antibody, 2F5, was used at 40 ng per well in the ELISA protocol described in this disclosure.

Absorbance readings twice above that of the negative control (0.07) were considered as positive.

TABLE IX

| Peptide | Sequence* | Isolate origin of V3 sequence | SEQ ID NO: |
|---|---|---|---|
| (P24N) | QMREPRGSDIAGTTSTL | | 70 |
| | ---- CLTB-56 ---- | | |
| CLTB-82 | QMREPRGSDIAGTTSTLNKRKRIHIGPGRAFYTTKN | MN | 71 |
| CLTB-85 | NKRKRIHIGPGRAFYTTKNQMREPRGSDIAGTTSTL | MN | 72 |
| (P24L) | EEMMTACQGVGGPGHK | | 73 |
| CLTB-83 | EEMMTACQGVGGPGHKNKRKRIHIGPGRAFYTTKN | MN | 74 |
| CLTB-87 | NKRKRIHIGPGRAFYTTKNEEMMTACQGVGGPGHK | MN | 75 |
| (P24M) | GHKARVLAEAMSQVT | | 76 |
| CLTB-84 | GHKARVLAEAMSQVTNKRKRIHIGPGRAFYTTKN | MN | 77 |
| CLTB-89 | NKRKRIHIGPGRAFYTTKNGHKARVLAEAMSQVT | MN | 78 |
| P24H | PIVQNIQGQMVHQAI | | 79 |
| | ------ PRI ------ | | |
| CLTB-156 | PIVQNIQGQMVHQAINTRKSIPIGPGRAFYTTG | Consensus of New York and Amsterdam | 80 |
| CLTB-157 | NTRKSIPIGPGRAFYTTGPIVQNIQGQMVHQAI | Consensus of New York and Amsterdam | 81 |
| T5 | YKYKVVKIEPLGVAP | | 82 |
| CLTB-158 | YKYKVVKIEPLGVAPNTRKSIPIGPGRAFYTTG | Consensus of New York and Amsterdam | 83 |
| CLTB-159 | NTRKSIPIGPGRAFYTTGYKYKVVKIEPLGVAP | Consensus of New York and Amsterdam | 84 |

*The V3 sequence used for the construction of the respective tandem epitope peptide is bolded whereas the T-cell epitope is shown in plain letters.

TABLE X

| Peptide | Sequence* | SEQ ID NO: |
|---|---|---|
| | ---- gp41 ---- | |
| CLTB-102 | GPKEPFRDYVDRFYKELLELDKWASLWNWFNKRKRIHIGPGRAFYTTKN | 85 |
| | ----- CLTB-56 ----- | |
| | ---- CLTB-56 ----- | |
| CLTB-103 | GPKEPFRDYVDRFYKNKRKRIHIGPGRAFYTTKNELLELDKWASLWNWF | 86 |
| | ---- gp41 ---- | |
| | ----- gp41 ---- | |
| CLTB-105 | ELLELDKWASLWNWFNKRKRIHIGPGRAFYTTKNGPKEPFRDYVDRFYK | 87 |
| | ---- CLTB-56 ----- | |
| | ----- CLTB-56 ----- | |
| CLTB-107 | NKRKRIHIGPGRAFYTTKNELLELDKWASLWNWFGPKEPFRDYVDRFYK | 88 |
| | ----- gp41 ---- | |
| | ---- MN-1 ----- | |
| T1-KAT4 | KQIINMWQEVEKAMYAKRIHIGPGRAFYTTKGPGELLELDKWASL | 89 |
| | --- gp41 -- | |
| | ---- MN-1 ---- | |
| P24E-KAT4 | GPKEPFRDYVDRFYKRIHIGPGRAFYTTKGPGELLELDKWASL | 90 |
| | --- gp41 -- | |
| CLTB-160 | ---- LIP ---- --- THAI --- ----- NYA ----- | |

TABLE X-continued

| Peptide | Sequence* | SEQ ID NO: |
|---|---|---|
| CLTB-161 | GPKEPFRDYVDRFYKKSIHIGPGKTLYAT<u>GPG</u>SITIGPGQVFYR<u>GPG</u>RKSIPIGPGRAFYTTG<br>----- LIP ----    --- THAI ---    ---- NYA ----<br>KQIINMWQEVEKAMYAKSIHIGPGKTLYAT<u>GPG</u>SITIGPGQVFYR<u>GPG</u>RKSIPIGPGRAFYTTG | 91<br><br>92 |

*The different V3 sequences incorporated into the respective construct are bolded. The isolate origin of the V3 sequences are indicated. For constructs, CLTB-160 and CLTB-161, LIP denotes a consensus for the London, India and Paris isolates; THAI denotes V3 of a Thailand HIV-1 virus; and NYA denotes a consensus of the primary isolates found in New York and Amsterdam. The T-cell, epitope, p24E and T1 are shown in plain letters.

TABLE XI

| Peptide | Sequence* | SEQ ID NO: |
|---|---|---|
| MPK-1 | KQIINMWQEVEKAMYAGPGELDKWASGPGGPKEPFRDYVDRFYK<br>----- T1-----   ---- p24E ----- | 94 |
| MPK-2 | GPKEPFRDYVDRFYKGPGELDKWASGPGKQIINMWQEVEKAMYA | 95 |
| MPK-3 | KQIINMWQEVEKAMYAGPGELDKWASGPGELDKWASGPGGPKEPFRDYVDRFYK | 96 |
| MPK-4 | GPKEPFRDYVDRFYKGPGELDKWASGPGELDKWASGPGKQIINMWQEVEKAMYA | 97 |

* The gp41 sequence used for the construction of the respective peptide is bolded whereas the T-cell epitopes, p24E and T1 are shown in plain letters. The linker sequence GPG is italisized.

TABLE XII

Functional activity of Murine and Guinea pig antisera raised against HIV-1(MN) peptides Reciprocal syncytia-blocking titre<sup>a)</sup>

| Antisera | Mouse | | Guinea pig | |
|---|---|---|---|---|
| | Freund's | Alum | Freund's | Alum |
| CLTB-36 | 10 | 60 | 90 | 40 |
| CLTB-37 | <10 | <10 | 10 | 10 |
| CLTB-56 | <10 | <10 | 10 | <10 |
| CLTB-34 | 10 | <10 | 20 | 40 |
| CLTB-35 | <10 | <10 | 10 | <10 |
| CLTB-55 | <10 | <10 | <10 | <10 |
| p24E-V3MN | 80 | <10 | 90 | <10 |
| V3MN-p24E | <10 | <10 | <10 | <10 |
| V3MN | <10 | <10 | <10 | <10 |
| CLTB-28 | <10 | <10 | 90 | <10 |
| CLTB-32 | <10 | <10 | <10 | <10 |
| CLTB-29 | <10 | <10 | <10 | <10 | a)The titres were based on > 90% inhibition of syncytia formation induced by the homologous HIV-1(MN) virus.

TABLE XIII

Immunogenicity of branched HIV-1 peptides.

| Immunizing Peptide | Reciprocal V3 (MN) peptide-specific antibody titre<sup>a)</sup> | | | |
|---|---|---|---|---|
| | Mouse | | Guinea Pig | |
| | Freund's | Alum | Freund's | Alum |
| CLTB-36 (MAP) | 12,150 | 12,150 | 24,300 | 12,150 |
| CLTB-34 (MAP) | NC | NC | 12,150 | 12,150 |
| CLTB-91 (MAP) | NC | NC | 24,300 | 8,100 |
| p24E-V3MN (MAP) | NC | NC | 24,300 | NC |
| VP-TB (MAP) | NC | NC | 2,700 | 2,700 | a)Results are expressed as mean reciprocal reactive titres against the respective BE-containing peptide (depicted in FIG. 1). Three guinea pigs and five mice were used for each determination.
NC: Not completed

TABLE XIV

Functional activity of antisera raised against branched peptides

| Immunizing Peptide | Reciprocal syncytia-blocking titre<sup>a)</sup> | | | |
|---|---|---|---|---|
| | Murine | | Guinea Pig | |
| | Freund's | Alum | Freund's | Alum |
| CLTB-36 (MAP) | >10 | >10 | 10 | 35 |
| CLTB-34 (MAP) | NC | NC | 20 | 40 |
| VP-TB (MAP) | NC | NC | 10 | 10 | a)Titres were based on > 90% inhibition of syncytia formation induced by the MN isolate.
NC: Not completed

REFERENCES

1. Spalding, B. J. Biotechnology 10: 24–29, 1992
2. Papsidero, L. P., Sheu, M. and Ruscetti, F. W. J. Virol. 63: 267–272, 1988
3. Sarin, P. S., Sun, D. K., Thornton, A. H. Naylor, P. H. and Goldstein, A. L. Science 232: 1135–1137, 1986
4. Palker, T. J. et al., J. of Immunol. 142: 3612–3619, 1989.
5. Gorny, M. K., Xu, J.-Y., Gianakakos, V., Karkowska, S., Williams, C., Sheppard, H. W., Hanson, C. V. and Zolla-Pasner, S. Proc. Natl. Acad. Sci., U.S.A., 88: 3238–3242, 1991
6. Buchacher, A. et al, AIDS Research and Human Retroviruses, 10: 359–369, 1994.
7. Skinner, M. A., Langlois, A. J., Mcdanal, C. B., McDougal, J. S., Bolognesi, D. and Matthews, T. J. J. Virol. 62: 4195–4200, 1988
8. Tam, J. P. Proc. Natl. Acad. Sci., U.S.A. 85: 5409–5413, 1988
9. Sondergard-Andersen, J. et al. Journal of Immunological Methods 131: 99–104, 1990
10. O'Hagan (1992), Clin. Pharmokinet 22:1
11. Ulmer et al (1993), Curr. Opinion Invest. Drugs 2(9) :983–989
12. Muster et al, (1993), J. of Virology, November 1993, pp. 6642–6647.

SEQUENCE LISTING ( 1 ) GENERAL INFORMATION:

( i i i ) NUMBER OF SEQUENCES: 101

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Gly  Pro  Gly  Arg
1
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Gly  Pro  Lys  Glu  Pro  Phe  Arg  Asp  Tyr  Val  Asp  Arg  Phe  Tyr  Lys
1                  5                        10                       15
```

( 2 ) INFORMATION FOR SEQ ID NO:3:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Gly  Pro  Lys  Glu  Pro  Phe  Arg  Asp  Tyr  Val  Asp  Arg  Phe  Tyr  Lys  Asn
1                  5                        10                       15

Lys  Arg  Lys  Arg  Ile  His  Ile  Gly  Pro  Gly  Arg  Ala  Phe  Tyr  Thr  Thr
                20                       25                       30

Lys  Asn
```

( 2 ) INFORMATION FOR SEQ ID NO:4:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Asn  Lys  Arg  Lys  Arg  Ile  His  Ile  Gly  Pro  Gly  Arg  Ala  Phe  Tyr  Thr
1                  5                        10                       15

Thr  Lys  Asn  Gly  Pro  Lys  Glu  Pro  Phe  Arg  Asp  Tyr  Val  Asp  Arg  Phe
                20                       25                       30

Tyr  Lys
```

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS: single ( D ) TOPOLOGY: linear ( x i ) SEQUENCE DESCRIPTION: SEQ ID NO:5:

```
Asn Lys Arg Lys Arg Ile His Ile Gly Pro Gly Arg Ala Phe Tyr Thr
1               5                   10                  15
Thr Lys Asn
```

( 2 ) INFORMATION FOR SEQ ID NO:6:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Gly Pro Lys Glu Pro Phe Arg Asp Tyr Val Asp Arg Phe Tyr Lys Arg
1               5                   10                  15
Lys Arg Ile His Ile Gly Pro Gly Arg Ala Phe Tyr Thr Thr Lys Asn
                20                  25                  30
```

( 2 ) INFORMATION FOR SEQ ID NO:7:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Arg Lys Arg Ile His Ile Gly Pro Gly Arg Ala Phe Tyr Thr Thr Lys
1               5                   10                  15
Asn Gly Pro Lys Glu Pro Phe Arg Asp Tyr Val Asp Arg Phe Tyr Lys
                20                  25                  30
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Arg Lys Arg Ile His Ile Gly Pro Gly Arg Ala Phe Tyr Thr Thr Lys
1               5                   10                  15
Asn
```

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Arg Lys Arg Ile His Ile Gly Pro Gly Arg Ala Phe Tyr Thr Thr Lys
1               5                   10                  15
Asn
```

( 2 ) INFORMATION FOR SEQ ID NO:10:

( i ) SEQUENCE CHARACTERISTICS:
        ( A ) LENGTH: 30 amino acids (B) TYPE: amino acid
(C) STRANDEDNESS: single
(D) TOPOLOGY: linear (xi) SEQUENCE DESCRIPTION: SEQ ID NO:10:

Arg Ile His Ile Gly Pro Gly Arg Ala Phe Tyr Thr Thr Lys Asn Gly
1               5                   10                  15
Pro Lys Glu Pro Phe Arg Asp Tyr Val Asp Arg Phe Tyr Lys
            20                  25                  30

(2) INFORMATION FOR SEQ ID NO:11:

(i) SEQUENCE CHARACTERISTICS:
    (A) LENGTH: 15 amino acids
    (B) TYPE: amino acid
    (C) STRANDEDNESS: single
    (D) TOPOLOGY: linear (xi) SEQUENCE DESCRIPTION: SEQ ID NO:11:

Arg Ile His Ile Gly Pro Gly Arg Ala Phe Tyr Thr Thr Lys Asn
1               5                   10                  15

(2) INFORMATION FOR SEQ ID NO:12:

(i) SEQUENCE CHARACTERISTICS:
    (A) LENGTH: 27 amino acids
    (B) TYPE: amino acid
    (C) STRANDEDNESS: single
    (D) TOPOLOGY: linear (xi) SEQUENCE DESCRIPTION: SEQ ID NO:12:

Gly Pro Lys Glu Pro Phe Arg Asp Tyr Val Asp Arg Phe Tyr Lys Arg
1               5                   10                  15
Lys Arg Ile His Ile Gly Pro Gly Arg Ala Phe
            20                  25

(2) INFORMATION FOR SEQ ID NO:13:

(i) SEQUENCE CHARACTERISTICS:
    (A) LENGTH: 27 amino acids
    (B) TYPE: amino acid
    (C) STRANDEDNESS: single
    (D) TOPOLOGY: linear (xi) SEQUENCE DESCRIPTION: SEQ ID NO:13:

Arg Lys Arg Ile His Ile Gly Pro Gly Arg Ala Phe Gly Pro Lys Glu
1               5                   10                  15
Pro Phe Arg Asp Tyr Val Asp Arg Phe Tyr Lys
            20                  25

(2) INFORMATION FOR SEQ ID NO:14:

(i) SEQUENCE CHARACTERISTICS:
    (A) LENGTH: 12 amino acids
    (B) TYPE: amino acid
    (C) STRANDEDNESS: single
    (D) TOPOLOGY: linear (xi) SEQUENCE DESCRIPTION: SEQ ID NO:14:

Arg Lys Arg Ile His Ile Gly Pro Gly Arg Ala Phe
1               5                   10

(2) INFORMATION FOR SEQ ID NO:15:

(i) SEQUENCE CHARACTERISTICS:
    (A) LENGTH: 36 amino acids
    (B) TYPE: amino acid ( C ) STRANDEDNESS: single
( D ) TOPOLOGY: linear ( x i ) SEQUENCE DESCRIPTION: SEQ ID NO:15:

Gly Pro Lys Glu Pro Phe Arg Asp Tyr Val Asp Arg Phe Tyr Lys Asn
1               5                   10                  15

Thr Arg Lys Ser Ile Arg Ile Gln Arg Gly Pro Gly Arg Ala Phe Tyr
            20              25                  30

Thr Thr Lys Asn
        35

( 2 ) INFORMATION FOR SEQ ID NO:16:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( x i ) SEQUENCE DESCRIPTION: SEQ ID NO:16:

Asn Thr Arg Lys Ser Ile Arg Ile Gln Arg Gly Pro Gly Arg Ala Phe
1               5                   10                  15

Tyr Thr Thr Lys Asn
            20

( 2 ) INFORMATION FOR SEQ ID NO:17:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( x i ) SEQUENCE DESCRIPTION: SEQ ID NO:17:

Asn Thr Arg Lys Ser Ile Arg Ile Gln Arg
1               5                   10

( 2 ) INFORMATION FOR SEQ ID NO:18:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( x i ) SEQUENCE DESCRIPTION: SEQ ID NO:18:

Gly Pro Gly Arg Ala Phe Tyr Thr Thr Lys Asn
1               5                   10

( 2 ) INFORMATION FOR SEQ ID NO:19:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( x i ) SEQUENCE DESCRIPTION: SEQ ID NO:19:

Gly Pro Lys Glu Pro Phe Arg Asp Tyr Val Asp Arg Phe Tyr Lys Cys
1               5                   10                  15

Thr Arg Pro Asn Tyr Asn Lys Arg Lys Arg Ile His Ile Gly Pro Gly
            20              25                  30

Arg Ala Phe Tyr Thr Thr Lys
        35

( 2 ) INFORMATION FOR SEQ ID NO:20:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

```
Cys  Thr  Arg  Pro  Asn  Tyr  Asn  Lys  Arg  Lys  Arg  Ile  His  Ile  Gly  Pro
1                   5                        10                       15

Gly  Arg  Ala  Phe  Tyr  Thr  Thr  Lys
               20
```

( 2 ) INFORMATION FOR SEQ ID NO:21:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

```
Lys  Gln  Ile  Ile  Asn  Met  Trp  Gln  Glu  Val  Glu  Lys  Ala  Met  Tyr  Ala
1                   5                        10                       15

Cys  Thr  Arg  Pro  Asn  Tyr  Asn  Lys  Arg  Lys  Arg  Ile  His  Ile  Gly  Pro
               20                       25                       30

Gly  Arg  Ala  Phe  Tyr  Thr  Thr  Lys
               35                  40
```

( 2 ) INFORMATION FOR SEQ ID NO:22:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:22:

```
Lys  Gln  Ile  Ile  Asn  Met  Trp  Gln  Glu  Val  Glu  Lys  Ala  Met  Tyr  Ala
1                   5                        10                       15
```

( 2 ) INFORMATION FOR SEQ ID NO:23:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

```
Lys  Gln  Ile  Ile  Asn  Met  Trp  Gln  Glu  Val  Glu  Lys  Ala  Met  Tyr  Ala
1                   5                        10                       15

Asn  Lys  Arg  Lys  Arg  Ile  His  Ile  Gly  Pro  Gly  Arg  Ala  Phe  Tyr  Thr
               20                       25                       30

Thr  Lys  Asn
          35
```

( 2 ) INFORMATION FOR SEQ ID NO:24:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( x i ) SEQUENCE DESCRIPTION: SEQ ID NO:24:

```
Gly Pro Lys Glu Pro Phe Arg Asp Tyr Val Asp Arg Phe Tyr Lys Asn
 1               5                  10                  15

Thr Arg Lys Ser Ile Tyr Ile Gly Pro Gly Arg Ala Phe His Thr Thr
                20                  25                  30

Gly Arg
```

(2) INFORMATION FOR SEQ ID NO:25:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:25:

```
Gly Pro Lys Glu Pro Phe Arg Asp Tyr Val Asp Arg Phe Tyr Lys Asn
 1               5                  10                  15

Thr Arg Lys Arg Ile Arg Ile Gln Arg Gly Pro Gly Arg Ala Phe Val
                20                  25                  30

Thr Ile Gly Lys
            35
```

(2) INFORMATION FOR SEQ ID NO:26:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO:26:

```
Gly Pro Lys Glu Pro Phe Arg Asp Tyr Val Asp Arg Phe Tyr Lys Asn
 1               5                  10                  15

Thr Arg Lys Ser Ile Thr Lys Gly Pro Gly Arg Val Ile Tyr Ala Thr
                20                  25                  30

Gly Gln
```

(2) INFORMATION FOR SEQ ID NO:27:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO:27:

```
Gly Pro Lys Glu Pro Phe Arg Asp Tyr Val Asp Arg Phe Tyr Lys Asn
 1               5                  10                  15

Thr Arg Gln Ser Thr Pro Ile Gly Leu Gly Gln Ala Leu Tyr Thr Thr
                20                  25                  30

Arg Gly
```

(2) INFORMATION FOR SEQ ID NO:28:

(i) SEQUENCE CHARACTERISTICS:
        (A) LENGTH: 40 amino acids
        (B) TYPE: amino acid
        (C) STRANDEDNESS: single
        (D) TOPOLOGY: linear (xi) SEQUENCE DESCRIPTION: SEQ ID NO:28:

```
Gly Pro Lys Glu Pro Phe Arg Asp Tyr Val Asp Arg Phe Tyr Lys Ser
 1               5                  10                  15
```

```
    Leu  Ile  Glu  Glu  Ser  Gln  Asn  Gln  Gln  Glu  Lys  Asn  Glu  Gln  Glu  Leu
                   20                      25                      30

Leu  Glu  Leu  Asp  Lys  Trp  Ala  Ser
                   35                      40
```

( 2 ) INFORMATION FOR SEQ ID NO: 29:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( x i ) SEQUENCE DESCRIPTION: SEQ ID NO: 29:

```
    Gly  His  Lys  Ala  Val  Leu  Ala  Glu  Met  Ser  Val  Thr  Asn  Lys  Arg  Lys
    1                   5                       10                      15

Arg  Ile  His  Ile  Gly  Pro  Gly  Arg  Ala  Phe  Tyr  Thr  Thr  Lys  Asn
                   20                      25                      30
```

( 2 ) INFORMATION FOR SEQ ID NO: 30:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO: 30:

```
    Gly  His  Lys  Ala  Arg  Val  Leu  Ala  Glu  Met  Ser  Gln  Val  Thr
    1                   5                       10
```

( 2 ) INFORMATION FOR SEQ ID NO: 31:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO: 31:

```
    Arg  Lys  Arg  Ile  His  Ile  Gly  Pro  Gly  Arg  Ala  Phe
    1                   5                       10
```

( 2 ) INFORMATION FOR SEQ ID NO: 32:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO: 32:

```
    Thr  Arg  Ser  Ile  His  Ile  Gly  Pro  Gly  Arg  Ala  Phe
    1                   5                       10
```

( 2 ) INFORMATION FOR SEQ ID NO: 33:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO: 33:

```
    Arg  Arg  Arg  Ile  His  Ile  Gly  Pro  Gly  Arg  Ala  Phe
    1                   5                       10
```

( 2 ) INFORMATION FOR SEQ ID NO: 34:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO: 34:

```
Arg Lys Ser Ile Tyr Ile Gly Pro Gly Arg Ala Phe
 1               5                  10
```

( 2 ) INFORMATION FOR SEQ ID NO: 35:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO: 35:

```
Lys Ser Ile Arg Ile Gln Arg Gly Pro Gly Arg Ala Phe Val Thr Ile
 1               5                  10                      15
Gly
```

( 2 ) INFORMATION FOR SEQ ID NO: 36:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO: 36:

```
Arg Lys Arg Ile Arg Ile Gln Arg Gly Pro Gly Arg Ala Phe
 1               5                  10
```

( 2 ) INFORMATION FOR SEQ ID NO: 37:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO: 37:

```
Arg Lys Ser Ile Thr Lys Gly Pro Gly Arg Val Ile Tyr Ala Thr
 1               5                  10                  15
```

( 2 ) INFORMATION FOR SEQ ID NO: 38:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO: 38:

```
Gly Pro Lys Glu Pro Phe Arg Asp Tyr Val Asp Arg Phe Tyr Lys Asn
 1               5                  10                      15
Thr Arg Lys Ser Ile Arg Ile Gln Arg Gly Pro Gly Arg Ala Phe Tyr
                20                  25                  30
Thr Ile Gly
        35
```

( 2 ) INFORMATION FOR SEQ ID NO: 39:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( x i ) SEQUENCE DESCRIPTION: SEQ ID NO: 39:

Gly Pro Lys Glu Pro Phe Arg Asp Tyr Val Asp Arg Phe Tyr Lys Asn
1               5                   10                  15

Thr Arg Lys Ser Ile Thr Lys Gly Pro Gly Arg Val Ile Tyr Ala Thr
            20              25                  30

Gly Gln Ile Ile Gly
            35

( 2 ) INFORMATION FOR SEQ ID NO: 40:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( x i ) SEQUENCE DESCRIPTION: SEQ ID NO: 40:

Gly Pro Lys Glu Pro Phe Arg Asp Tyr Val Asp Arg Phe Tyr Lys Asn
1               5                   10                  15

Lys Arg Lys Arg Ile His Ile Gly Pro Gly Arg Val Ile Tyr Ala Thr
            20              25                  30

Gly Gln Ile Ile Gly
            35

( 2 ) INFORMATION FOR SEQ ID NO: 41:

( i ) SEQUENCE CHARACTERISTICS:
    ( A ) LENGTH: 33 amino acids
    ( B ) TYPE: amino acid
    ( C ) STRANDEDNESS: single
    ( D ) TOPOLOGY: linear ( x i ) SEQUENCE DESCRIPTION: SEQ ID NO: 41:

Gly Pro Lys Glu Pro Phe Arg Asp Tyr Val Asp Arg Phe Tyr Lys Asn
1               5                   10                  15

Thr Arg Lys Ser Ile Pro Ile Gly Pro Gly Arg Ala Phe Tyr Thr Thr
            20              25                  30

Gly ( 2 ) INFORMATION FOR SEQ ID NO: 42:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( x i ) SEQUENCE DESCRIPTION: SEQ ID NO: 42:

Gly Pro Lys Glu Pro Phe Arg Asp Tyr Val Asp Arg Phe Tyr Lys Asn
1               5                   10                  15

Thr Arg Lys Arg Ile His Met Gly Pro Gly Arg Ala Phe Tyr Ala Thr
            20              25                  30

Gly Asp Ile Ile Gly
            35

( 2 ) INFORMATION FOR SEQ ID NO: 43:

( i ) SEQUENCE CHARACTERISTICS:
  ( A ) LENGTH: 38 amino acids
  ( B ) TYPE: amino acid
  ( C ) STRANDEDNESS: single
  ( D ) TOPOLOGY: linear ( x i ) SEQUENCE DESCRIPTION: SEQ ID NO: 43:

Gly Pro Lys Glu Pro Phe Arg Asp Tyr Val Asp Arg Phe Tyr Lys Asn
1               5                   10                  15

Thr Arg Lys Ser Ile His Ile Gly Pro Gly Arg Ala Phe Tyr Thr Thr
            20              25                  30

Gly Glu Ile Ile Gly Cys
            35

( 2 ) INFORMATION FOR SEQ ID NO: 44:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( x i ) SEQUENCE DESCRIPTION: SEQ ID NO: 44:

Gly Pro Lys Glu Pro Phe Arg Asp Tyr Val Asp Arg Phe Tyr Lys Asn
1               5                   10                  15

Thr Arg Lys Ser Ile His Ile Gly Pro Gly Arg Ala Phe Tyr Ala Thr
            20              25                  30

Gly Glu Ile Ile Gly
            35

( 2 ) INFORMATION FOR SEQ ID NO: 45:

( i ) SEQUENCE CHARACTERISTICS:
    ( A ) LENGTH: 34 amino acids
    ( B ) TYPE: amino acid
    ( C ) STRANDEDNESS: single
    ( D ) TOPOLOGY: linear ( x i ) SEQUENCE DESCRIPTION: SEQ ID NO: 45:

Lys Gln Ile Ile Asn Met Trp Gln Glu Val Glu Lys Ala Met Tyr Ala
1               5                   10                  15

Asn Thr Arg Lys Ser Ile Pro Ile Gly Pro Gly Arg Ala Phe Tyr Thr
            20              25                  30

Thr Gly ( 2 ) INFORMATION FOR SEQ ID NO: 46:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: linear ( x i ) SEQUENCE DESCRIPTION: SEQ ID NO: 46:

Lys Gln Ile Ile Asn Met Trp Gln Glu Val Glu Lys Ala Met Tyr Ala
1               5                   10                  15

Asn Thr Arg Lys Gly Ile His Ile Gly Pro Gly Arg Ala Phe Tyr Thr
            20              25                  30

Gly Glu Ile Val Gly Asp Ile Arg Gln
            35              40

( 2 ) INFORMATION FOR SEQ ID NO: 47:

( i ) SEQUENCE CHARACTERISTICS:

(A) LENGTH: 32 amino acids
(B) TYPE: amino acid
(C) STRANDEDNESS: single
(D) TOPOLOGY: linear (xi) SEQUENCE DESCRIPTION: SEQ ID NO: 47:

Gly His Lys Ala Arg Val Leu Ala Glu Ala Met Ser Gln Val Thr Asn
1               5                   10                  15
Thr Lys Arg Ser Ile Pro Ile Gly Pro Gly Arg Ala Phe Tyr Thr Gly
            20              25                  30

(2) INFORMATION FOR SEQ ID NO: 48:

(i) SEQUENCE CHARACTERISTICS:
(A) LENGTH: 22 amino acids
(B) TYPE: amino acid
(C) STRANDEDNESS: single
(D) TOPOLOGY: linear (xi) SEQUENCE DESCRIPTION: SEQ ID NO: 48:

Asn Thr Arg Lys Arg Ile His Met Gly Pro Gly Arg Ala Phe Tyr Ala
1               5                   10                  15
Thr Gly Asp Ile Ile Gly
            20

(2) INFORMATION FOR SEQ ID NO: 49:

(i) SEQUENCE CHARACTERISTICS:
(A) LENGTH: 25 amino acids
(B) TYPE: amino acid
(C) STRANDEDNESS: single
(D) TOPOLOGY: linear (xi) SEQUENCE DESCRIPTION: SEQ ID NO: 49:

Asn Thr Arg Lys Gly Ile His Ile Gly Pro Gly Arg Ala Phe Tyr Thr
1               5                   10                  15
Gly Glu Ile Val Gly Asp Ile Arg Gln
            20              25

(2) INFORMATION FOR SEQ ID NO: 50:

(i) SEQUENCE CHARACTERISTICS:
(A) LENGTH: 18 amino acids
(B) TYPE: amino acid
(C) STRANDEDNESS: single
(D) TOPOLOGY: linear (xi) SEQUENCE DESCRIPTION: SEQ ID NO: 50:

Asn Thr Arg Lys Ser Ile Pro Ile Gly Pro Gly Arg Ala Phe Tyr Thr
1               5                   10                  15
Thr Gly (2) INFORMATION FOR SEQ ID NO: 51:

(i) SEQUENCE CHARACTERISTICS:
(A) LENGTH: 20 amino acids
(B) TYPE: amino acid
(C) STRANDEDNESS: single
(D) TOPOLOGY: linear (xi) SEQUENCE DESCRIPTION: SEQ ID NO: 51:

Asn Thr Arg Lys Ser Ile Arg Ile Gln Arg Gly Pro Gly Arg Ala Phe
1               5                   10                  15
Tyr Thr Ile Gly
            20

( 2 ) INFORMATION FOR SEQ ID NO: 52:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( x i ) SEQUENCE DESCRIPTION: SEQ ID NO: 52:

```
Asn Thr Arg Lys Ser Ile Thr Lys Gly Pro Gly Arg Val Ile Tyr Ala
 1               5                  10                  15
Thr Gly Gln Ile Ile Gly
            20
```

( 2 ) INFORMATION FOR SEQ ID NO: 53:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( x i ) SEQUENCE DESCRIPTION: SEQ ID NO: 53:

```
Asn Lys Arg Lys Arg Ile His Ile Gly Pro Gly Arg Val Ile Tyr Ala
 1               5                  10                  15
Thr Gly Gln Ile Ile Gly
            20
```

( 2 ) INFORMATION FOR SEQ ID NO: 54:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO: 54:

```
Gly Pro Lys Glu Pro Phe Arg Asp Tyr Val Asp Arg Phe Tyr Lys Glu
 1               5                  10                  15
Gln Glu Leu Leu Glu Leu Asp Lys Trp Ala Ser Leu Trp Asn Trp Phe
            20                  25                  30
Asp Ile Thr
        35
```

( 2 ) INFORMATION FOR SEQ ID NO: 55:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO: 55:

```
Glu Gln Glu Leu Leu Glu Leu Asp Lys Trp Ala Ser Leu Trp Asn Trp
 1               5                  10                  15
Phe Asp Ile Thr
        20
```

( 2 ) INFORMATION FOR SEQ ID NO: 56:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( x i ) SEQUENCE DESCRIPTION: SEQ ID NO: 56:

Gly Pro Lys Glu Pro Phe Arg Asp Tyr Val Asp Arg Phe Tyr Lys Glu
1               5                   10                  15

Leu Leu Glu Leu Asp Lys Trp Ala Ser Leu Trp Asn Trp Phe Asp Ile
            20                  25                  30

Thr ( 2 ) INFORMATION FOR SEQ ID NO: 57:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( x i ) SEQUENCE DESCRIPTION: SEQ ID NO: 57:

Glu Leu Leu Glu Leu Asp Lys Trp Ala Ser Leu Trp Asn Trp Phe Asp
1               5                   10                  15

Ile Thr ( 2 ) INFORMATION FOR SEQ ID NO: 58:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( x i ) SEQUENCE DESCRIPTION: SEQ ID NO: 58:

Gly Pro Lys Glu Pro Phe Arg Asp Tyr Val Asp Arg Phe Tyr Lys Glu
1               5                   10                  15

Leu Asp Lys Trp Ala Ser Leu Trp Asn Trp Phe Asp Ile Thr
            20                  25                  30

( 2 ) INFORMATION FOR SEQ ID NO: 59:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( x i ) SEQUENCE DESCRIPTION: SEQ ID NO: 59:

Glu Leu Asp Lys Trp Ala Ser Leu Trp Asn Trp Phe Asp Ile Thr
1               5                   10                  15

( 2 ) INFORMATION FOR SEQ ID NO: 60:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( x i ) SEQUENCE DESCRIPTION: SEQ ID NO: 60:

Gly Pro Lys Glu Pro Phe Arg Asp Tyr Val Asp Arg Phe Tyr Lys Glu
1               5                   10                  15

Gln Glu Leu Leu Glu Leu Asp Lys Trp Ala Ser Leu Trp Asn Trp Phe
            20                  25                  30

( 2 ) INFORMATION FOR SEQ ID NO: 61:

( i ) SEQUENCE CHARACTERISTICS:
    ( A ) LENGTH: 17 amino acids
    ( B ) TYPE: amino acid (C) STRANDEDNESS: single
(D) TOPOLOGY: linear (xi) SEQUENCE DESCRIPTION: SEQ ID NO: 61:

Glu Gln Glu Leu Leu Glu Leu Asp Lys Trp Ala Ser Leu Trp Asn Trp
1               5                   10                  15
Phe (2) INFORMATION FOR SEQ ID NO: 62:

(i) SEQUENCE CHARACTERISTICS:
 (A) LENGTH: 30 amino acids
 (B) TYPE: amino acid
 (C) STRANDEDNESS: single
 (D) TOPOLOGY: linear (xi) SEQUENCE DESCRIPTION: SEQ ID NO: 62:

Gly Pro Lys Glu Pro Phe Arg Asp Tyr Val Asp Arg Phe Tyr Lys Glu
1               5                   10                  15
Leu Leu Glu Leu Asp Lys Trp Ala Ser Leu Trp Asn Trp Phe
            20                  25                  30

(2) INFORMATION FOR SEQ ID NO: 63:

(i) SEQUENCE CHARACTERISTICS:
 (A) LENGTH: 27 amino acids
 (B) TYPE: amino acid
 (C) STRANDEDNESS: single
 (D) TOPOLOGY: linear (xi) SEQUENCE DESCRIPTION: SEQ ID NO: 63:

Gly Pro Lys Glu Pro Phe Arg Asp Tyr Val Asp Arg Phe Tyr Lys Glu
1               5                   10                  15
Leu Asp Lys Trp Ala Ser Leu Trp Asn Trp Phe
            20                  25

(2) INFORMATION FOR SEQ ID NO: 64:

(i) SEQUENCE CHARACTERISTICS:
 (A) LENGTH: 26 amino acids
 (B) TYPE: amino acid
 (C) STRANDEDNESS: single
 (D) TOPOLOGY: linear (xi) SEQUENCE DESCRIPTION: SEQ ID NO: 64:

Gly Pro Lys Glu Pro Phe Arg Asp Tyr Val Asp Arg Phe Tyr Lys Glu
1               5                   10                  15
Gln Glu Leu Leu Glu Leu Asp Lys Trp Ala
            20                  25

(2) INFORMATION FOR SEQ ID NO: 65:

(i) SEQUENCE CHARACTERISTICS:
 (A) LENGTH: 24 amino acids
 (B) TYPE: amino acid
 (C) STRANDEDNESS: single
 (D) TOPOLOGY: linear (xi) SEQUENCE DESCRIPTION: SEQ ID NO: 65:

Gly Pro Lys Glu Pro Phe Arg Asp Tyr Val Asp Arg Phe Tyr Lys Glu
1               5                   10                  15
Leu Leu Glu Leu Asp Lys Trp Ala
            20

(2) INFORMATION FOR SEQ ID NO: 66:

( i ) SEQUENCE CHARACTERISTICS:
  ( A ) LENGTH: 33 amino acids
  ( B ) TYPE: amino acid
  ( C ) STRANDEDNESS: single
  ( D ) TOPOLOGY: linear ( x i ) SEQUENCE DESCRIPTION: SEQ ID NO: 66:

Lys Gln Ile Ile Asn Met Trp Gln Glu Val Glu Lys Ala Met Tyr Ala
1               5                   10                  15

Glu Gln Glu Leu Leu Glu Leu Asp Lys Trp Ala Ser Leu Trp Asn Trp
            20              25                  30

Phe ( 2 ) INFORMATION FOR SEQ ID NO: 67:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( x i ) SEQUENCE DESCRIPTION: SEQ ID NO: 67:

Lys Gln Ile Ile Asn Met Trp Gln Glu Val Glu Lys Ala Met Tyr Ala
1               5                   10                  15

Glu Leu Asp Lys Trp Ala Ser
            20

( 2 ) INFORMATION FOR SEQ ID NO: 68:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( x i ) SEQUENCE DESCRIPTION: SEQ ID NO: 68:

Lys Gln Ile Ile Asn Met Trp Gln Glu Val Glu Lys Ala Met Tyr Ala
1               5                   10                  15

Gly Pro Gly Glu Leu Leu Glu Leu Asp Lys Trp Ala Ser Leu
            20              25                  30

( 2 ) INFORMATION FOR SEQ ID NO: 69:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( x i ) SEQUENCE DESCRIPTION: SEQ ID NO: 69:

Glu Leu Asp Lys Trp Ala
1               5

( 2 ) INFORMATION FOR SEQ ID NO: 70:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( x i ) SEQUENCE DESCRIPTION: SEQ ID NO: 70:

Gln Met Arg Glu Pro Arg Gly Ser Asp Ile Ala Gly Thr Thr Ser Thr
1               5                   10                  15

Leu ( 2 ) INFORMATION FOR SEQ ID NO: 71:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( x i ) SEQUENCE DESCRIPTION: SEQ ID NO: 71:

```
Gln Met Arg Glu Pro Arg Gly Ser Asp Ile Ala Gly Thr Thr Ser Thr
 1               5                  10                  15

Leu Asn Lys Arg Lys Arg Ile His Ile Gly Pro Gly Arg Ala Phe Tyr
            20                  25                  30

Thr Thr Lys Asn
            35
```

( 2 ) INFORMATION FOR SEQ ID NO: 72:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( x i ) SEQUENCE DESCRIPTION: SEQ ID NO: 72:

```
Asn Lys Arg Lys Arg Ile His Ile Gly Pro Gly Arg Ala Phe Tyr Thr
 1               5                  10                  15

Thr Lys Asn Gln Met Arg Glu Pro Arg Gly Ser Asp Ile Ala Gly Thr
            20                  25                  30

Thr Ser Thr Leu
            35
```

( 2 ) INFORMATION FOR SEQ ID NO: 73:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO: 73:

```
Glu Glu Met Met Thr Ala Cys Gln Gly Val Gly Gly Pro Gly His Lys
 1               5                  10                  15
```

( 2 ) INFORMATION FOR SEQ ID NO: 74:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO: 74:

```
Glu Glu Met Met Thr Ala Cys Gln Gly Val Gly Gly Pro Gly His Lys
 1               5                  10                  15

Asn Lys Arg Lys Arg Ile His Ile Gly Pro Gly Arg Ala Phe Tyr Thr
            20                  25                  30

Thr Lys Asn
            35
```

( 2 ) INFORMATION FOR SEQ ID NO: 75:

( i ) SEQUENCE CHARACTERISTICS:
        ( A ) LENGTH: 35 amino acids (B) TYPE: amino acid
(C) STRANDEDNESS: single
(D) TOPOLOGY: linear (xi) SEQUENCE DESCRIPTION: SEQ ID NO: 75:

Asn Lys Arg Lys Arg Ile His Ile Gly Pro Gly Arg Ala Phe Tyr Thr
1               5                   10                  15
Thr Lys Asn Glu Glu Met Met Thr Ala Cys Gln Gly Val Gly Gly Pro
            20                  25                  30
Gly His Lys
        35

(2) INFORMATION FOR SEQ ID NO: 76:

(i) SEQUENCE CHARACTERISTICS:
    (A) LENGTH: 15 amino acids
    (B) TYPE: amino acid
    (C) STRANDEDNESS: single
    (D) TOPOLOGY: linear (xi) SEQUENCE DESCRIPTION: SEQ ID NO: 76:

Gly His Lys Ala Arg Val Leu Ala Glu Ala Met Ser Gln Val Thr
1               5                   10                  15

(2) INFORMATION FOR SEQ ID NO: 77:

(i) SEQUENCE CHARACTERISTICS:
    (A) LENGTH: 34 amino acids
    (B) TYPE: amino acid
    (C) STRANDEDNESS: single
    (D) TOPOLOGY: linear (xi) SEQUENCE DESCRIPTION: SEQ ID NO: 77:

Gly His Lys Ala Arg Val Leu Ala Glu Ala Met Ser Gln Val Thr Asn
1               5                   10                  15
Lys Arg Lys Arg Ile His Ile Gly Pro Gly Arg Ala Phe Tyr Thr Thr
            20                  25                  30
Lys Asn (2) INFORMATION FOR SEQ ID NO: 78:

(i) SEQUENCE CHARACTERISTICS:
    (A) LENGTH: 34 amino acids
    (B) TYPE: amino acid
    (C) STRANDEDNESS: single
    (D) TOPOLOGY: linear (xi) SEQUENCE DESCRIPTION: SEQ ID NO: 78:

Asn Lys Arg Lys Arg Ile His Ile Gly Pro Gly Arg Ala Phe Tyr Thr
1               5                   10                  15
Thr Lys Asn Gly His Lys Ala Arg Val Leu Ala Glu Ala Met Ser Gln
            20                  25                  30
Val Thr (2) INFORMATION FOR SEQ ID NO: 79:

(i) SEQUENCE CHARACTERISTICS:
    (A) LENGTH: 15 amino acids
    (B) TYPE: amino acid
    (C) STRANDEDNESS: single
    (D) TOPOLOGY: linear (xi) SEQUENCE DESCRIPTION: SEQ ID NO: 79:

Pro Ile Val Gln Asn Ile Gln Gly Gln Met Val His Gln Ala Ile
1               5                   10                  15

( 2 ) INFORMATION FOR SEQ ID NO: 80:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( x i ) SEQUENCE DESCRIPTION: SEQ ID NO: 80:

```
Pro Ile Val Gln Asn Ile Gln Gly Gln Met Val His Gln Ala Ile Asn
 1               5                  10                  15
Thr Arg Lys Ser Ile Pro Ile Gly Pro Gly Arg Ala Phe Tyr Thr Thr
             20                  25                  30
Gly
```

( 2 ) INFORMATION FOR SEQ ID NO: 81:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( x i ) SEQUENCE DESCRIPTION: SEQ ID NO: 81:

```
Asn Thr Arg Lys Ser Ile Pro Ile Gly Pro Gly Arg Ala Phe Tyr Thr
 1               5                  10                  15
Thr Gly Pro Ile Val Gln Asn Ile Gln Gly Gln Met Val His Gln Ala
             20                  25                  30
Ile
```

( 2 ) INFORMATION FOR SEQ ID NO: 82:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO: 82:

```
Tyr Lys Tyr Lys Val Val Lys Ile Glu Pro Leu Gly Val Ala Pro
 1               5                  10                  15
```

( 2 ) INFORMATION FOR SEQ ID NO: 83:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( x i ) SEQUENCE DESCRIPTION: SEQ ID NO: 83:

```
Tyr Lys Tyr Lys Val Val Lys Ile Glu Pro Leu Gly Val Ala Pro Asn
 1               5                  10                  15
Thr Arg Lys Ser Ile Pro Ile Gly Pro Gly Arg Ala Phe Tyr Thr Thr
             20                  25                  30
Gly
```

( 2 ) INFORMATION FOR SEQ ID NO: 84:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( x i ) SEQUENCE DESCRIPTION: SEQ ID NO: 84:

Asn Thr Arg Lys Ser Ile Pro Ile Gly Pro Gly Arg Ala Phe Tyr Thr
1               5                   10                  15

Thr Gly Tyr Lys Tyr Lys Val Val Lys Ile Glu Pro Leu Gly Val Ala
                20              25                  30

Pro ( 2 ) INFORMATION FOR SEQ ID NO: 85:

( i ) SEQUENCE CHARACTERISTICS:
      ( A ) LENGTH: 49 amino acids
      ( B ) TYPE: amino acid
      ( C ) STRANDEDNESS: single
      ( D ) TOPOLOGY: linear ( x i ) SEQUENCE DESCRIPTION: SEQ ID NO: 85:

Gly Pro Lys Glu Pro Phe Arg Asp Tyr Val Asp Arg Phe Tyr Lys Glu
1               5                   10                  15

Leu Leu Glu Leu Asp Lys Trp Ala Ser Leu Trp Asn Trp Phe Asn Lys
                20              25                  30

Arg Lys Arg Ile His Ile Gly Pro Gly Arg Ala Phe Tyr Thr Thr Lys
            35                  40                  45

Asn ( 2 ) INFORMATION FOR SEQ ID NO: 86:

( i ) SEQUENCE CHARACTERISTICS:
      ( A ) LENGTH: 49 amino acids
      ( B ) TYPE: amino acid
      ( C ) STRANDEDNESS: single
      ( D ) TOPOLOGY: linear ( x i ) SEQUENCE DESCRIPTION: SEQ ID NO: 86:

Gly Pro Lys Glu Pro Phe Arg Asp Tyr Val Asp Arg Phe Tyr Lys Asn
1               5                   10                  15

Lys Arg Lys Arg Ile His Ile Gly Pro Gly Arg Ala Phe Tyr Thr Thr
                20              25                  30

Lys Asn Glu Leu Leu Glu Leu Asp Lys Trp Ala Ser Leu Trp Asn Trp
            35                  40                  45

Phe ( 2 ) INFORMATION FOR SEQ ID NO: 87:

( i ) SEQUENCE CHARACTERISTICS:
      ( A ) LENGTH: 49 amino acids
      ( B ) TYPE: amino acid
      ( C ) STRANDEDNESS: single
      ( D ) TOPOLOGY: linear ( x i ) SEQUENCE DESCRIPTION: SEQ ID NO: 87:

Glu Leu Leu Glu Leu Asp Lys Trp Ala Ser Leu Trp Asn Trp Phe Asn
1               5                   10                  15

Lys Arg Lys Arg Ile His Ile Gly Pro Gly Arg Ala Phe Tyr Thr Thr
                20              25                  30

Lys Asn Gly Pro Lys Glu Pro Phe Arg Asp Tyr Val Asp Arg Phe Tyr
            35                  40                  45

Lys ( 2 ) INFORMATION FOR SEQ ID NO: 88:

( i ) SEQUENCE CHARACTERISTICS:
    ( A ) LENGTH: 49 amino acids
    ( B ) TYPE: amino acid
    ( C ) STRANDEDNESS: single
    ( D ) TOPOLOGY: linear ( x i ) SEQUENCE DESCRIPTION: SEQ ID NO: 88:

Asn Lys Arg Lys Arg Ile His Ile Gly Pro Gly Arg Ala Phe Tyr Thr
1               5                   10                  15

Thr Lys Asn Glu Leu Leu Glu Leu Asp Lys Trp Ala Ser Leu Trp Asn
            20                  25                  30

Trp Phe Gly Pro Lys Glu Pro Phe Arg Asp Tyr Val Asp Arg Phe Tyr
        35                  40                  45

Lys ( 2 ) INFORMATION FOR SEQ ID NO: 89:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( x i ) SEQUENCE DESCRIPTION: SEQ ID NO: 89:

Lys Gln Ile Ile Asn Met Trp Gln Glu Val Glu Lys Ala Met Tyr Ala
1               5                   10                  15

Lys Arg Ile His Ile Gly Pro Gly Arg Ala Phe Tyr Thr Thr Lys Gly
            20                  25                  30

Pro Gly Glu Leu Leu Glu Leu Asp Lys Trp Ala Ser Leu
        35                  40                  45

( 2 ) INFORMATION FOR SEQ ID NO: 90:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( x i ) SEQUENCE DESCRIPTION: SEQ ID NO: 90:

Gly Pro Lys Glu Pro Phe Arg Asp Tyr Val Asp Arg Phe Tyr Lys Arg
1               5                   10                  15

Ile His Ile Gly Pro Gly Arg Ala Phe Tyr Thr Thr Lys Gly Pro Gly
            20                  25                  30

Glu Leu Leu Glu Leu Asp Lys Trp Ala Ser Leu
        35                  40

( 2 ) INFORMATION FOR SEQ ID NO: 91:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( x i ) SEQUENCE DESCRIPTION: SEQ ID NO: 91:

Gly Pro Lys Glu Pro Phe Arg Asp Tyr Val Asp Arg Phe Tyr Lys Lys
1               5                   10                  15

Ser Ile His Ile Gly Pro Gly Lys Thr Leu Tyr Ala Thr Gly Pro Gly
            20                  25                  30

Ser Ile Thr Ile Gly Pro Gly Gln Val Phe Tyr Arg Gly Pro Gly Arg
        35                  40                  45

Lys Ser Ile Pro Ile Gly Pro Gly Arg Ala Phe Tyr Thr Thr Gly ( 2 ) INFORMATION FOR SEQ ID NO: 92:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( x i ) SEQUENCE DESCRIPTION: SEQ ID NO: 92:

```
Lys Gln Ile Ile Asn Met Trp Gln Glu Val Glu Lys Ala Met Tyr Ala
1               5                   10                  15
Lys Ser Ile His Ile Gly Pro Gly Lys Thr Leu Tyr Ala Thr Gly Pro
            20                  25                  30
Gly Ser Ile Thr Ile Gly Pro Gly Gln Val Phe Tyr Arg Gly Pro Gly
            35                  40                  45
Arg Lys Ser Ile Pro Ile Gly Pro Gly Arg Ala Phe Tyr Thr Thr Gly
        50                  55                  60
```

( 2 ) INFORMATION FOR SEQ ID NO: 93:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO: 93:

```
Glu Leu Leu Glu Leu Asp Lys Trp Ala Ser Leu Trp Asn Trp Phe
1               5                   10                  15
```

( 2 ) INFORMATION FOR SEQ ID NO: 94:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( x i ) SEQUENCE DESCRIPTION: SEQ ID NO: 94:

```
Lys Gln Ile Ile Asn Met Trp Gln Glu Val Glu Lys Ala Met Tyr Ala
1               5                   10                  15
Gly Pro Gly Glu Leu Asp Lys Trp Ala Ser Gly Pro Gly Gly Pro Lys
            20                  25                  30
Glu Pro Phe Arg Asp Tyr Val Asp Arg Phe Tyr Lys
            35                  40
```

( 2 ) INFORMATION FOR SEQ ID NO: 95:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( x i ) SEQUENCE DESCRIPTION: SEQ ID NO: 95:

```
Gly Pro Lys Glu Pro Phe Arg Asp Tyr Val Asp Arg Phe Tyr Lys Gly
1               5                   10                  15
Pro Gly Glu Leu Asp Lys Trp Ala Ser Gly Pro Gly Lys Gln Ile Ile
            20                  25                  30
Asn Met Trp Gln Glu Val Glu Lys Ala Met Tyr Ala
            35                  40
```

( 2 ) INFORMATION FOR SEQ ID NO: 96:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( x i ) SEQUENCE DESCRIPTION: SEQ ID NO: 96:

```
Lys Gln Ile Ile Asn Met Trp Gln Glu Val Glu Lys Ala Met Tyr Ala
 1               5                  10                  15

Gly Pro Gly Glu Leu Asp Lys Trp Ala Ser Gly Pro Gly Glu Leu Asp
                 20                  25                  30

Lys Trp Ala Ser Gly Pro Gly Gly Pro Lys Glu Pro Phe Arg Asp Tyr
             35                  40                  45

Val Asp Arg Phe Tyr Lys
             50
```

( 2 ) INFORMATION FOR SEQ ID NO: 97:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( x i ) SEQUENCE DESCRIPTION: SEQ ID NO: 97:

```
Gly Pro Lys Glu Pro Phe Arg Asp Tyr Val Asp Arg Phe Tyr Lys Gly
 1               5                  10                  15

Pro Gly Glu Leu Asp Lys Trp Ala Ser Gly Pro Gly Glu Leu Asp Lys
                 20                  25                  30

Trp Ala Ser Gly Pro Gly Lys Gln Ile Ile Asn Met Trp Gln Glu Val
             35                  40                  45

Glu Lys Ala Met Tyr Ala
             50
```

( 2 ) INFORMATION FOR SEQ ID NO: 98:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO: 98:

```
Glu Leu Asp Lys Trp Ala Ser
 1               5
```

( 2 ) INFORMATION FOR SEQ ID NO:99:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( x i ) SEQUENCE DESCRIPTION: SEQ ID NO:99:

```
Asn Thr Arg Lys Ser Ile Arg Ile Gln Arg Gly Pro Gly Arg Ala Phe
 1               5                  10                  15

Val Thr Ile Gly Lys Ile Gly Cys
                 20
```

( 2 ) INFORMATION FOR SEQ ID NO:100:

( i ) SEQUENCE CHARACTERISTICS:

(A) LENGTH: 19 amino acids
(B) TYPE: amino acid
(C) STRANDEDNESS: single
(D) TOPOLOGY: linear (xi) SEQUENCE DESCRIPTION: SEQ ID NO:100:

Asn Thr Arg Lys Ser Ile Tyr Ile Gly Pro Gly Arg Ala Phe His Thr
1               5                   10                  15

Thr Gly Arg (2) INFORMATION FOR SEQ ID NO:101:

(i) SEQUENCE CHARACTERISTICS:
(A) LENGTH: 19 amino acids
(B) TYPE: amino acid
(C) STRANDEDNESS: single
(D) TOPOLOGY: linear (xi) SEQUENCE DESCRIPTION: SEQ ID NO:101:

Asn Thr Arg Lys Ser Ile Thr Lys Gly Pro Gly Arg Val Ile Tyr Ala
1               5                   10                  15

Thr Gly Gln

What we claim is:

1. A synthetic peptide molecule having a plurality of individual linear synthetic peptides linked at the C-terminus of each said individual linear synthetic peptides to form a multimeric molecule, each said individual linear synthetic peptides having an amino acid sequence containing a T-cell epitope of a gag or envelope protein of a human immunodeficiency virus (HIV) isolate linked to an amino acid sequence containing a B-cell epitope of a gag or envelope protein of an HIV isolate.

2. The synthetic peptide molecule of claim 1 wherein each synthetic peptide in said multimeric molecule is the same.

3. The synthetic peptide molecule of claim 1 wherein said individual linear synthetic peptides are selected from the group consisting of:

(a) a synthetic peptide having at least one amino acid sequence containing a T-cell epitope of the gag protein of a human immunodeficiency virus (HIV) isolate linked at the N-terminal or C-terminal end thereof, to at least one amino acid sequence containing a B-cell epitope of the V3 loop of the envelope protein of an HIV isolate, wherein, when located at said N-terminal end, said B-cell epitope containing sequence and said T-cell epitope containing sequence are directly coupled; and (b) a synthetic peptide having at least one amino acid sequence containing a T-cell epitope of the gag protein of a human immunodeficiency virus (HIV) isolate linked at the N-terminal or C-terminal end thereof, to at least one amino acid sequence containing a B-cell epitope of the gp41 protein of an HIV isolate comprising the sequence $X_1LKDWX_2$ wherein $X_1$ is E, A, G or Q and $X_2$ is A or T or a sequence capable of eliciting an HIV-specific antiserum and recognizing the sequence $X_1LKDWX_2$.

4. The synthetic peptide molecule of claim 1 wherein said multimeric molecule is:

[GPKEPFRDYVDRFYKNKRKRIHIGPGRAFYTTKN]$_4$.

5. The synthetic peptide molecule of claim 1 wherein said multimeric molecule is:

[GPKEPFRDYVDRFYKRKRIHIGPGRAFYTTKN]$_4$.

6. The synthetic peptide molecule of claim 1 wherein said multimeric molecule is:

[GPKEPFRDYVDRFYKNTRKSIRIQRGPGRAFYTTKN]$_4$.

7. The synthetic peptide molecule of claim 1 wherein said multimeric molecule is:

[KQIINWQEVEKAMYANKRKRIHIGPGRAFYTTKN]$_4$.

8. The synthetic peptide molecule of claim 1 wherein said multimeric molecule is:

[GPKEPFRDYVDRFYKRIHIGPGRAFYTTKN]$_4$.

9. An immunogenic composition, comprising at least one synthetic peptide as claimed in claim 1, and a pharmaceutically-acceptable carrier therefor.

* * * * *